US008241475B2

(12) United States Patent
Gunnarsson et al.

(10) Patent No.: US 8,241,475 B2
(45) Date of Patent: Aug. 14, 2012

(54) TWO-DIMENSIONAL STRANDNESS-AND LENGTH-DEPENDENT SEPARATION OF NUCLEIC ACID FRAGMENTS

(75) Inventors: Gudmundur H. Gunnarsson, Reykjavik (IS); Hans Guttormur Thormar, Reykjavik (IS); Bjarki Gudmundsson, Kopanogur (IS); Jon Johannes Jonsson, Reykjavik (IS)

(73) Assignee: Lifeind ehf., Reykjavik (IS)

( * ) Notice: Subject to any disclaimer, the term of this patent is extended or adjusted under 35 U.S.C. 154(b) by 1241 days.

(21) Appl. No.: 11/661,607

(22) PCT Filed: Sep. 2, 2005

(86) PCT No.: PCT/IS2005/000019
§ 371 (c)(1),
(2), (4) Date: Oct. 2, 2007

(87) PCT Pub. No.: WO2006/025074
PCT Pub. Date: Mar. 9, 2006

(65) Prior Publication Data
US 2009/0107841 A1    Apr. 30, 2009

(30) Foreign Application Priority Data
Sep. 2, 2004  (IS) .............................. 7436

(51) Int. Cl.
*G01N 27/447* (2006.01)
*G01N 27/453* (2006.01)

(52) U.S. Cl. ......... 204/461; 204/466; 204/612; 204/616

(58) Field of Classification Search .......... 204/456–458, 204/465–467, 606–609, 616–618
See application file for complete search history.

(56) References Cited

U.S. PATENT DOCUMENTS

| 5,074,980 A | * | 12/1991 | Vasta-Russell et al. ...... 204/461 |
| 5,162,514 A | * | 11/1992 | Serwer et al. ............... 435/91.52 |
| 5,212,299 A | * | 5/1993 | Smith ........................... 536/114 |

(Continued)

FOREIGN PATENT DOCUMENTS
WO      WO-97/30062 A1    8/1997
(Continued)

OTHER PUBLICATIONS

Matsubara et al. Biochim. Biophys. Acta, 55 (1962) 392-395.*
Anderson et al., "The TYCHO system for computer analysis of two-dimensional gel electrophoresis patterns," Clinical Chemistry, Nov. 1981, vol. 27, No. 11, pp. 1807-1820.
Anderson, "Detection, sequence patterns and function of unusual DNA structures," Nucleic Acids Research, Nov. 11, 1986, vol. 14, No. 21, pp. 8513-8533.

(Continued)

*Primary Examiner* — Alex Noguerola
(74) *Attorney, Agent, or Firm* — Birch Stewart Kolasch & Birch, LLP

(57) ABSTRACT

A method is provided for separating single- and double-stranded nucleic acid molecules based on their strandness and length. The method is based on novel two-dimensional gel electrophoresis techniques comprises loading a sample of nucleic acid molecules in a gel electrophoresis apparatus and electrophoresing in a first dimension said sample through a gel matrix under a first set of pre-determined electrophoresis conditions; electrophoresing said gel matrix in a second dimension under a second set of electrophoresis conditions, such that populations of single- and double-stranded nucleic acids are separated, said first and second electrophoresis conditions being different, such that in one dimension electrophoresis allows separation of the sample molecules based on strandness and length, and in the other dimension electrophoresis allows separation based substantially on length, wherein said difference is established with a chemical agent and/or physical parameter affecting the strandness-dependent electrophoresis migration rate of nucleic acids.

29 Claims, 12 Drawing Sheets

U.S. PATENT DOCUMENTS

| | | |
|---|---|---|
| 6,210,931 B1 | 4/2001 | Feldstein et al. |
| 2003/0124611 A1 | 7/2003 | Schwartz |
| 2004/0005614 A1 * | 1/2004 | Kurn et al. .................. 435/6 |
| 2004/0129567 A1 | 7/2004 | Auton et al. |

FOREIGN PATENT DOCUMENTS

| | | |
|---|---|---|
| WO | WO 97/30152 A1 * | 8/1997 |
| WO | WO-97/39149 A | 10/1997 |
| WO | WO-02/10182 A1 | 2/2002 |
| WO | WO 03/058230 A1 | 7/2003 |
| WO | WO-03/070943 A1 | 8/2003 |

OTHER PUBLICATIONS

Kovar et al., "Two dimensional single-strand conformation polymorphism analysis: a useful tool for the detection of mutations in long DNA fragments," Nucleic Acids Research, vol. 19, No. 13, Jul. 11, 1991, pp. 3507-3510.

Mizuno, "Random cloning of bent DNA segments from *Escherichia coli* chromosome and primary characterization of their structures," Nucleic Acids Research, Sep. 11, 1987, vol. 15, No. 17, pp. 6827-6841.

* cited by examiner (a)

(b) 5 min (c) 30 min (d) 180 min (e)

TWO-DIMENSIONAL STRANDNESS-AND LENGTH-DEPENDENT SEPARATION OF NUCLEIC ACID FRAGMENTS

FIELD OF THE INVENTION

The present invention is in the field of screening simple and complex preparations of nucleic acid fragments (DNA, RNA and DNA/RNA hybrids). The method separates single- and double stranded fragments, in a length-independent manner. Within each group fragments are separated according to their length. After the separation, fragments can be isolated and further characterized. Examples of applicability include, but are not limited to: I) estimation of renaturation efficiency for complex nucleic acid samples, II) detection and isolation of DNA fragments that contain single-stranded breaks, III) estimation of the amount and the length distribution of both single- and double-stranded nucleic acids in biological samples, IV) quality assessment of nucleic acid preparations including PCR products and other in vitro amplification products, and VI) estimation of EDNA synthesis efficiency and the existence of RNA:DNA hybrids in complex mixtures.

BACKGROUND OF THE INVENTION

Nucleic acids can be divided, according to their strandness, into two major groups comprising single-stranded (ss) or double-stranded (ds) molecules. RNA molecules are most often single-stranded, but the local folding of the polymer chain can result in intra-strand duplexes of different kinds. DNA molecules are usually double-stranded, where the strands are complementary, and form a double helix. Double-stranded nucleic acid molecules are formed by reversible non-covalent interaction between the two strands. The reversibility of complementary binding of nucleic acid strands is crucial for semi-conservative replication of the genetic material and for gene expression.

Analyses of nucleic acids in vitro often rely on their strandness. For example, measurement of renaturation for nucleic acids depends on the ability to monitor the transition from single- to double-stranded form. Further, due to the reversibility of the double-helix, in vitro conditions may facilitate the conversion of double-stranded nucleic acid molecules to single-stranded molecules, or vice versa. Renaturation is an important step in many different methods of molecular biology (e.g. hybridization, PCR and cDNA normalization). It is therefore of great importance to have simple and efficient methods to estimate the strandness of nucleic acid preparations.

A few methods have been described to estimate the amount or to separate/isolate single-stranded and double-stranded nucleic acids from a complex mixture of both. During denaturation or renaturation the transition between single- and double-stranded forms can be monitored by observing changes in UV light absorption due to the hypochromatic effect. The ratio of red to green fluorescence of acridine orange reflects the levels of single- and double-stranded nucleic acids but this ratio also depends on factors such as salt concentration and dye-to-nucleic acid ratio (McMaster and Carmichael 1977; Spano, Bonde et al. 2000). These two methods only allow estimation of the ratio between the single- and double-stranded forms, but they cannot be used for physical separation and isolation of either fraction. They can also not be used to analyse the association between strandness and length of nucleic acid fragments in complex preparations. The strong binding-preference of double-over single-stranded nucleic acids to hydroxyapatite allows the physical separation of single- and double-stranded nucleic acids (Sambrook and Russell 2001). The double-stranded fraction isolated based on the strong hydroxyapatite binding may also contain fragments that are partially single-stranded or completely single-stranded but with local folding resulting in formation of double-stranded structures (e.g. hairpins). Nuclease degradation of single-stranded nucleic acids is often used to discriminate between single- and double-stranded forms in a complex mixture of both. Here only the double-stranded fraction can be recovered and it may contain single-stranded nucleic acids with local double-stranded structures such as stem loops. A major limitation of nuclease degradation is the non-specificity i.e. double-stranded nucleic acids are also nicked and degraded to various extents.

None of the methods described above provide any direct information about the length composition of single-stranded or double-stranded nucleic acid fractions. Further, only the hydroxyapatite method allows isolation of both the single-stranded and double-stranded nucleic acid fractions.

Double-stranded nucleic acid fragments (>50 bp) generally have higher migration velocity than their single-stranded counterparts in polyacrylamide-gel electrophoresis (PAGE). Therefore, double-stranded and single-stranded fragments of equal length will migrate differently and resolve in one-dimensional electrophoresis. This well-known phenomenon has been utilized in e.g. combined heteroduplex/single-stranded-conformation polymorphisms methods (Ravnik-Glavac, Glavac et al. 1994; Sainz, Huynh et al. 1994). All one-dimensional electrophoresis methods based on strandness-dependent separation are limited to samples that contain only a few nucleic acid fragments. If a sample contains many nucleic acid fragments of different lengths, long double-stranded fragments may co-migrate and overlap with shorter single-stranded fragments and thus the population of double-stranded fragments cannot be resolved from the population of single-stranded fragments. This has precluded the use of gel electrophoresis to monitor the strandness of complex nucleic acid preparations.

Methods for separating individual nucleic acid fragments from a complex mixture based on their difference in strandness would be of great interest. Such methods would be much more versatile and powerful if they could be used to simultaneously analyze length distribution of the single- and the double-stranded fractions. Examples where such methods could be used include but are not limited to: I) physical separation of single-stranded and double-stranded nucleic acids fragments allowing, quantification or isolation of either class, II) estimation of the relative amount and length distribution of both single- and double-stranded nucleic acids in biological samples, III) measurement of renaturation kinetics by time-point analysis, IV) isolation of double-stranded nucleic acid fragments containing single-stranded breaks from bulk amount of intact molecules, V) to monitor quality of complex nucleic acid preparations including PCR products and other in vitro amplification products, VI) estimation of cDNA synthesis efficiency and the existence of RNA:DNA hybrids in complex mixtures, and VII) to monitor efficiency of labelling complex nucleic acid samples.

Genetic information is encoded by the linear sequence of bases in a nucleic acid strand. The term "strandness" of nucleic acid molecule is herein used to describe the number of nucleic acid strands are in each nucleic acid molecule. A nucleic acid strand is composed of linear covalently linked poly-nucleotides. Most frequently nucleic acid molecules are single- stranded or double-stranded wherein the double-stranded molecule is formed by reversible intermolecular hydrogen bonding between two single-stranded nucleic acid molecules. In some cases nucleic acid can be multi-stranded e.g. triple helixes or quartets.

As used herein the term "conformation" describes the global 3D structure of nucleic acid molecules. Identical single-stranded nucleic acid molecules can have various different conformations due to e.g. intramolecular hydrogen bonding and folding. Different local intramolecular secondary structures of single-stranded nucleic acids can also affect conformation; hence such differences also fall under the term conformational differences as used herein. Conformational diversity is much more constrained in double-stranded of nucleic acids. Although strandness can affect the overall conformation of nucleic acid molecules, current methods to separate molecules according to conformation cannot by used to separate complex nucleic acid mixtures according to strandness.

The inventors have previously developed a physicochemical method, two-dimensional conformation dependent electrophoresis (2D-CDE) (see, EP 1476549). The method allows separation of double-stranded DNA fragments according to their conformation as well as their length. 2D-CDE is therefore not suitable for separation according to strandness as it is designed for conformational separation of double-stranded nucleic acid molecules. Further conformational differences of double-stranded molecules are ideally enhanced or induced during the first dimension of 2D-CDE while strandness-dependent separation should ideally reduce or eliminate conformational differences within both single- or double-stranded fractions respectively, to ensure separation only according to strandness and length.

Kovar et al. have described a method for "Two dimensional single-strand conformation polymorphism analysis" (Kovar, Jug et al. 1991). The first dimension is carried out under denaturing conditions in order to prevent folding (all double-stranded DNA molecules are made single-stranded). All fragments are therefore single-stranded and migrate strongly according to length as the denaturating condition reduces different conformational variation of each single-stranded nucleic acid molecule. The first dimension is carried out in a capillary electrophoresis system. After the first dimension the capillary gel matrix is laid onto a non-denaturating polyacrylamide gel matrix in a horizontal gel electrophoresis system. During the second dimension electrophoresis all nucleic acid molecules are single-stranded as in the first dimension. Due to lack of denaturating agents in the second dimension the single-stranded molecules can adapt various conformations and the separation will by according to both fold-back conformation and length. The method can however not be used to separate single- and double-stranded linear nucleic acid molecules. The method only allows separation according to different length and fold-back conformation of single-stranded fragments.

SUMMARY OF INVENTION

The present invention provides methods to achieve strandness- and length-dependent separation of nucleic acid fragments based on a novel two-dimensional (2D) gel electrophoresis system. The two-dimensional strandness- and length-dependent electrophoresis method and system (for which the acronym 2D-SDE is used herein) separates nucleic acid fragments based both on length and strandness in one dimension but only according to length in the second dimension. The system is capable of separating a population of single-stranded fragments from a population of double-stranded fragments in a complex mixture of both and allows the determination of the length-distribution within each population. The system further provides the option of isolating either or both fractions.

An ideal 2D-SDE system is preferably based on a single gel-matrix eliminating the troublesome transfer between two different gel-matrixes. A physical or chemical factor can then be introduced (or removed) after the first dimension to affect the strandness of all nucleic acid fragments in such way that all molecules migrate in the second dimension electrophoresis in the same length-dependent manner, independent from their original strandness in the original sample.

Many chemical factors have been reported to affect the strandness of nucleic acid fragments, including but not limited to denaturing agents such as formamide, urea, and DMSO. Physical factors such as temperature can also be used. Combinations of both chemical and physical factors are often used to ensure effective denaturation.

The methods of the invention can be applied to nucleic acid fragments obtained from different sources and they do not require any special prior manipulation of the nucleic acid fragments.

The present invention provides general methods that can be used in different contexts such as but not limited to: I) physical separation of single-stranded and double-stranded nucleic acid fragments allowing quantification and/or isolation of either one or both classes, II) estimation of the amount and length distribution of both single- and double-stranded nucleic acids in biological samples, III) measurement of renaturation kinetics, IV) isolation of double-stranded nucleic acid fragments containing single-stranded breaks from bulk amount of intact fragments, V) monitoring quality of complex nucleic acid preparations including PCR and other in vitro amplification products, VI) estimation of cDNA synthesis efficiency and the existence of RNA:DNA hybrids in complex mixtures, and VII) to monitor efficiency of labelling complex nucleic samples.

The method of the invention utilizes a novel two-dimensional strandness-dependent electrophoresis system (2D-SDE). In the first dimension, single- and double-stranded nucleic acid fragments of equal length migrate at different rates. After the first dimension separation, the gel-matrix is treated with a physical and/or chemical agent to allow complete denaturation (strand-separation) of the double-stranded nucleic acid molecules. The second dimension is then run preferably perpendicular to the first dimension. Running the second dimension at 90° to the first dimension offers greatest resolution although other angles could be used. In the second dimension nucleic acid fragments are separated only according to their length because they are now all in the single-stranded form.

The 2D-SDE system results in the separation of all nucleic acid fragments based on their strandness. In each population of single- and double-stranded nucleic acids, all fragments are separated according to their length. Migration velocities of single-stranded nucleic acid fragments are the same in both dimensions, as local intramolecular secondary structures of single-stranded nucleic acid fragments are minimized in the first dimension. This results in formation of a diagonal line of nucleic acid fragments of varying length that are single-stranded in both dimensions. Migration velocity of nucleic acid fragments that are originally double-stranded is different between the two dimensions (double-stranded migration velocity in the first is relatively faster than the single-stranded migration velocity in the second). The difference in relative migration velocity is length-dependent. This difference results in formation of an arc that is separated from and placed behind the diagonal line of the originally single-stranded nucleic acid fragments. After separation, both nucleic acid fragment fractions can be quantified in the gel or isolated.

Single-stranded nucleic acid fragments migrate essentially only according to their length in PAGE if the gel contains a denaturing chemical agent in sufficiently high concentration. For example, urea strongly reduces secondary structures of ssDNA fragments in PAGE (Viovy 2000). This behaviour of single-stranded nucleic acids fragments is used in common techniques of DNA sequencing. Under such conditions, ssDNA fragments behave as flexible linear polyelectrolytes, allowing separation according to the length of the molecule (Tinland, Pernodet et al. 1996).

Although the addition of a denaturing chemical agent, such as urea, strongly reduces secondary structures of single-stranded nucleic acids fragments, double-stranded nucleic acid fragments are not denatured (strands separated). Therefore, the addition of a denaturing agent allows both single-stranded fragments and double-stranded fragments to migrate essentially according to their length but not with the same length-dependent migration factor, i.e. single- and double-stranded fragments of equal length do not co-migrate.

1A: Cy5-labeled (green) DNA fragments were untreated and thus remained double-stranded while Cy3-labeled fragments were denatured to single-stranded form. Double-stranded (green) fragments formed an arc 2, while single-stranded (red) fragments formed a diagonal line 1. Separation was performed in 10% PAGE containing 7 M urea.

1B: Both the Cy5-labeled fragments and Cy3-labeled fragments were denatured to single-stranded form and co-migrated to form a yellow diagonal line 3.

1C: Both Cy5- and Cy3-labeled DNA fragments were left untreated and co-migrated to form a yellow arc 4. A small fraction of DNA fragments migrated as would be expected for single-stranded DNA fragments. This was most likely due to partial reannealing of denatured double-stranded DNA fragments in the system before the second dimension electrophoresis. This fraction was not seen when the experiment was repeated conducting the second dimension separation was at 55° C. (not shown).

Figure 2:
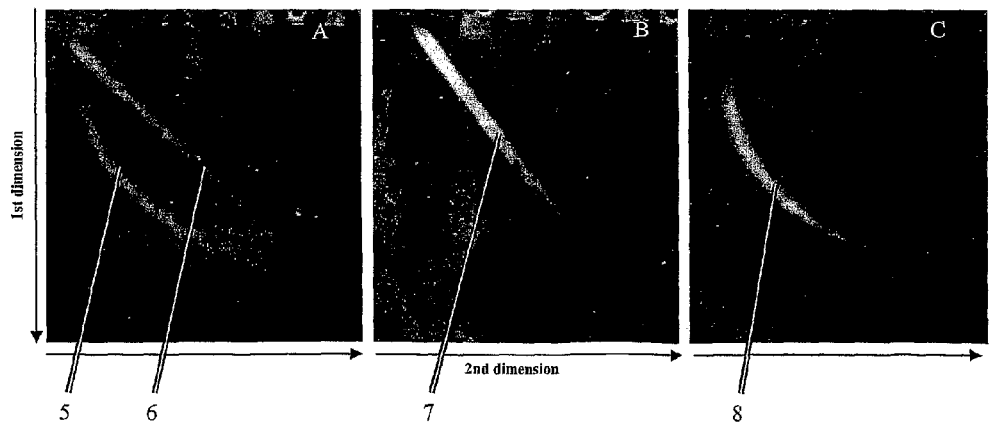

FIG. 2. Fluorescent image of 2D-SDE gel analyses as described in Example 2. 2D-SDE was used to separate single-stranded DNA and double-stranded DNA fragments representing the human genome.

2A: A pool of untreated (double-stranded) Cy5-labeled (green) genomic DNA fragments and denatured Cy3-labeled (red) genomic DNA fragments was electrophoresed. Single-stranded DNA fragments (red) formed a diagonal line 6 and were separated from double-stranded DNA fragments (green) that formed an arc 5.

2B: A pool of denatured (single-stranded) Cy5- and Cy3-labeled DNA fragments was electrophoresed. All DNA fragments co-migrated in a single diagonal line 7, which shows as yellow in the original gel.

2C: Both Cy5- and Cy3-labeled DNA fragments were untreated (double-stranded) and co-migrated to form an arc 8 which is colored yellow in the original gel.

Figure 3:
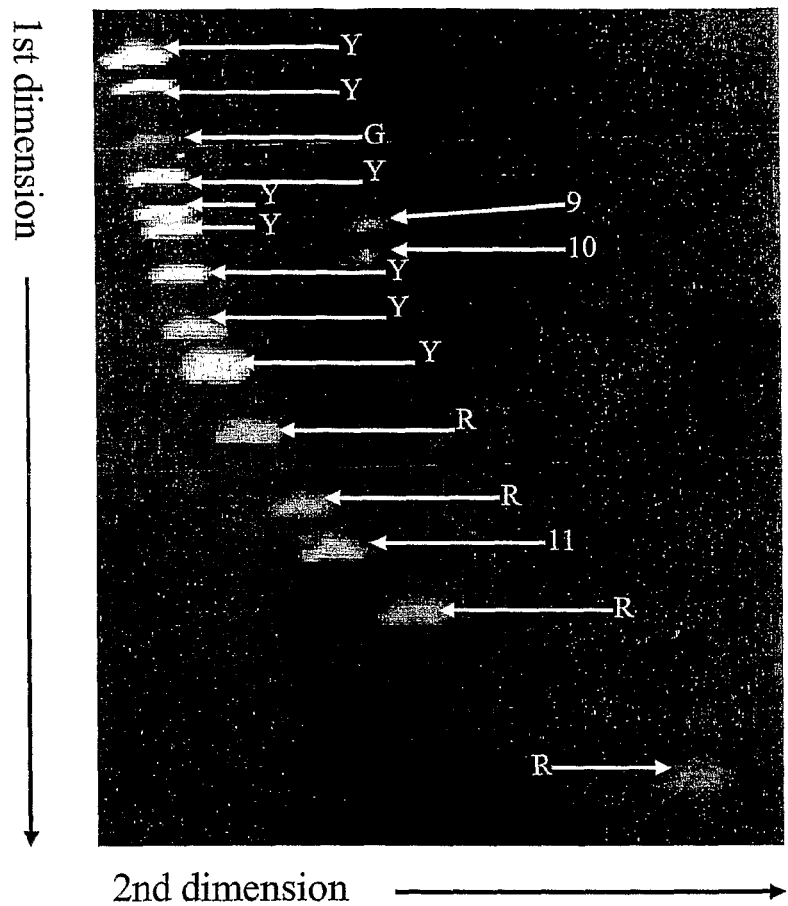

FIG. 3. Fluorescent image of an EtBr-stained PAGE gel from a 2D-SDE analysis used to separate bulge-containing heteroduplexes from a mixture of 14 perfectly matched DNA fragments, as described in Example 3. A 274 bp long PCR product was amplified from individual having a 9 bp deletion in one allele of exon 11 in the C-kit gene. The PCR resulted in formation of two bulge-containing heteroduplexes and two homoduplexes. The PCR product was mixed with sample of 14 perfectly matched DNA fragments and separated using 2D-SDE. The two heteroduplexes (9, 10, green in figure) migrated in front of the arc representing the perfectly matched Cy5-labeled double-stranded DNA fragments. Cy5-labeled fragments are red in figure (R) or yellow (Y) if the fragments were long enough to stain heavily with EtBr. The homoduplexes generated in the PCR reaction (11, green in gel) migrated as expected in the arc of the 14 Cy5-labeled perfectly matched DNA fragments.

Figure 4:
Figure 4:
Figure 4:
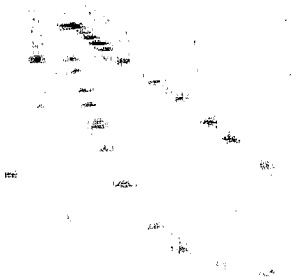
Figure 4:
Figure 4:
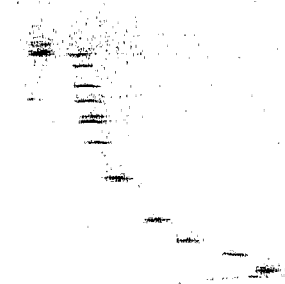

FIG. 4. 2D-SDE separation of samples from different time points of the renaturation reaction described in Example 4. After denaturation (a), only the diagonal line representing the single-stranded DNA fragments was detected. With longer renaturation time (indicated in minutes), density of the arc representing the double-stranded DNA fragments increased. Untreated DNA mixture gave rise to an arc representing double-stranded DNA fragments shown in (e).

Figure 5:
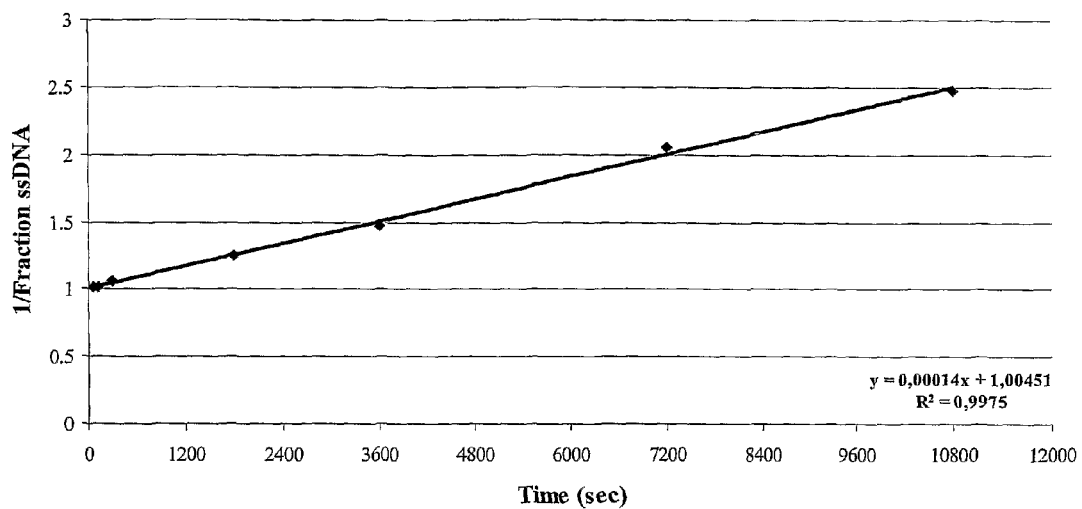

FIG. 5. Second order plot for renaturation reaction conducted as described in Example 4 showing on the y-axis 1/Fraction ssDNA as a function of time. The plot reveals a strong linear relationship of the data and therefore reflects a second order kinetics expected of the renaturation reaction. Same slope was observed when the data for the last time point (68,400 sec) was included.

Figure 6:
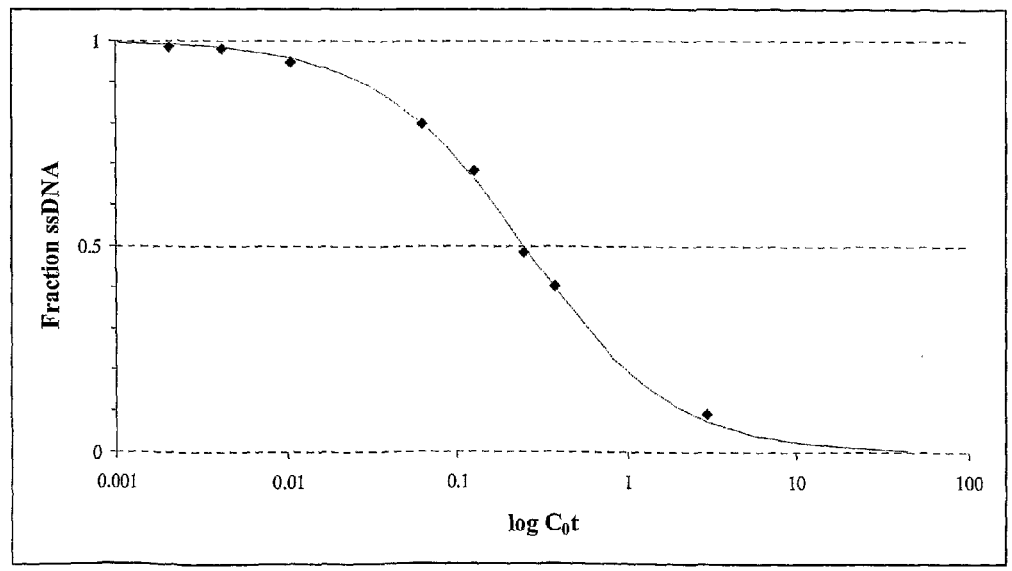

FIG. 6. Renaturation kinetics of the DNA fragments assayed by 2D-SDE as described in Example 4. Data points obtained from the renaturation reaction are presented as diamonds (♦). After solving the ideal second order equation for C using the observed k the ideal $C_0 t$ curve was obtained (plotted as red line). $C_0$=total molar DNA phosphate concentration, t=time in seconds.

Figure 7:
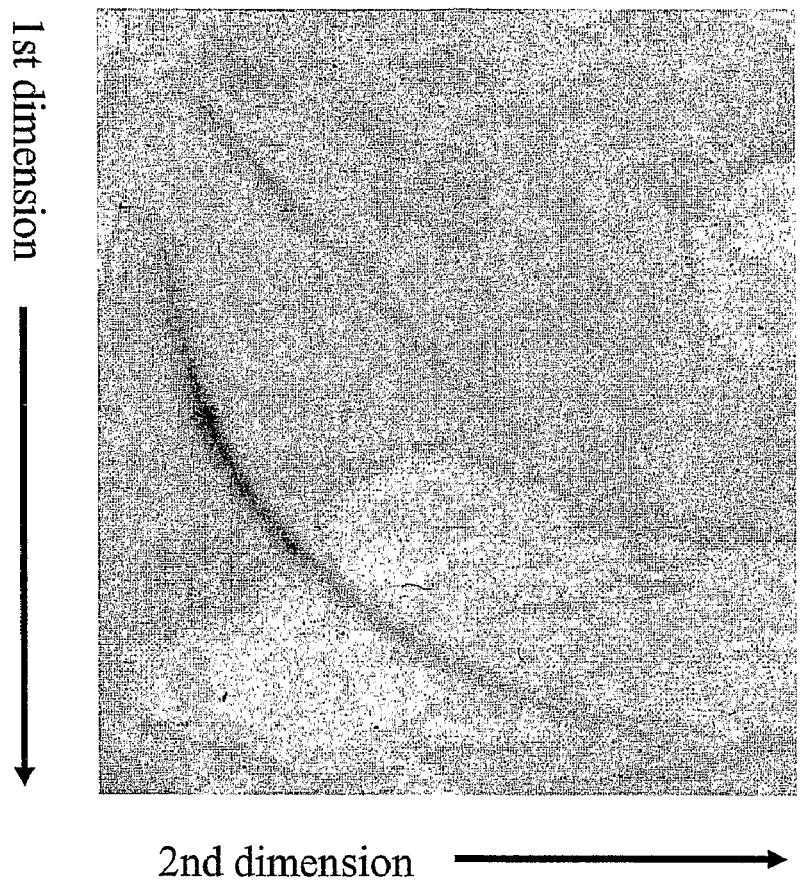

FIG. 7. Fluorescent image of 2D-SDE analysis to estimate quality of complex PCR reactions, conducted as described in Example 9. Unlabeled products from a complex PCR reaction were separated using 2D-SDE. The gel was stained with EtBr after the separation. Both the arc representing double-stranded DNA fragments and the line representing ssDNA fragments were obtained. This indicates considerable amount of ssDNA products in the complex PCR reaction. Note that EtBr stains longer DNA fragments more intensely than the shorter ones.

Figure 8:
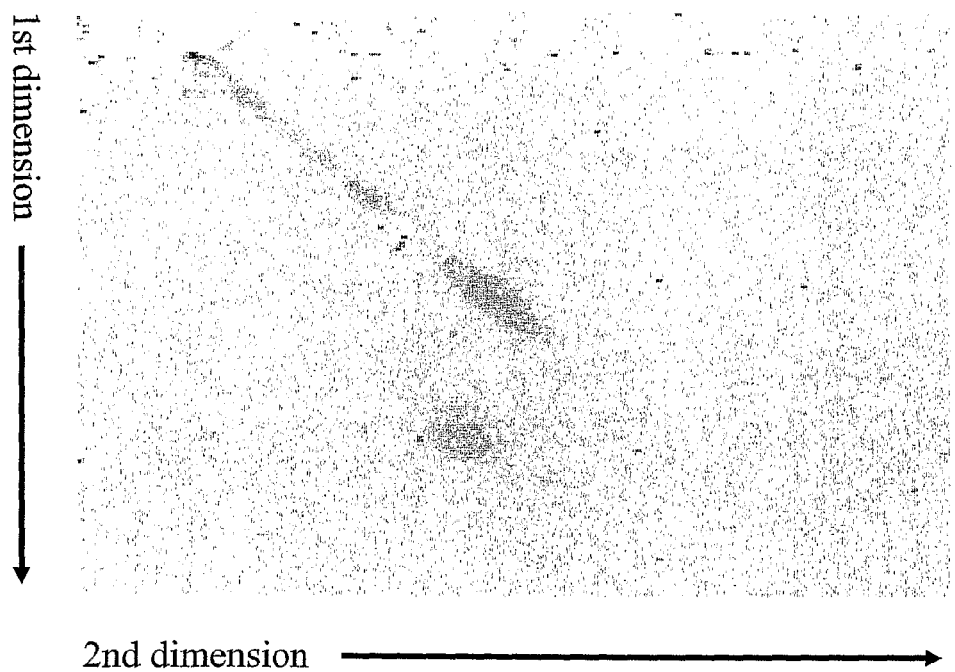

FIG. 8. Fluorescent image of 2D-SDE analysis used to reveal the structure of uncharacterized DNA isolated from plasma of healthy adults, conducted as described in Example 10. Both single-stranded and double-stranded DNA fragments were detected.

Figure 9:
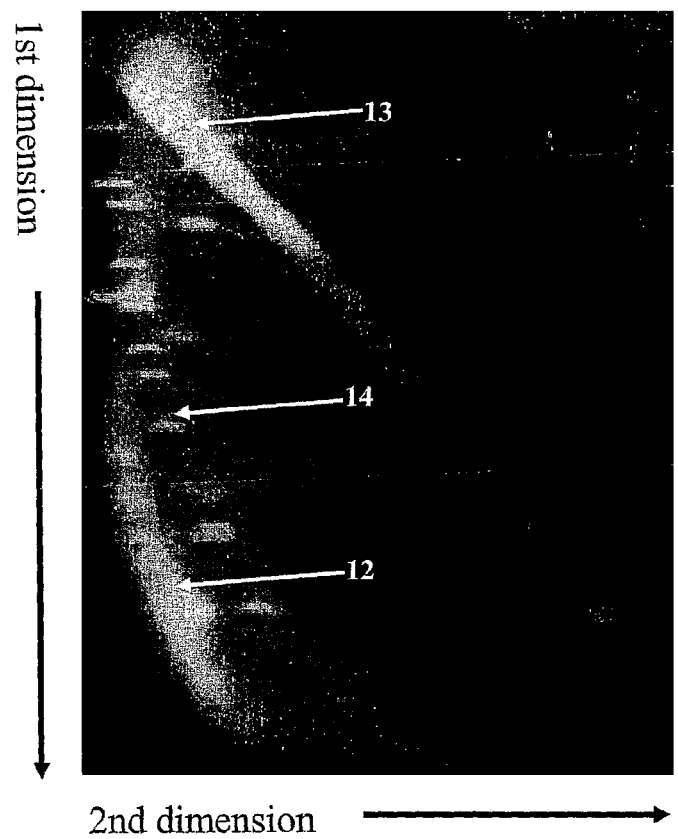

FIG. 9. Fluorescent image of 2D-SDE analysis used to reveal the efficiency of the first strand cDNA synthesis, conducted as described in Example 11. After the first strand synthesis of cDNA using Cy5-labeled dCTP (green) the products were mixed with unlabeled 100 bp double-stranded DNA ladder from Fermentas (red). Two green arcs/lines were obtained representing the RNA:DNA hybrids (12) and the single-stranded DNA fraction (13). One red arc (14) was obtained representing the EtBr stained double-stranded DNA ladder.

Figure 10:
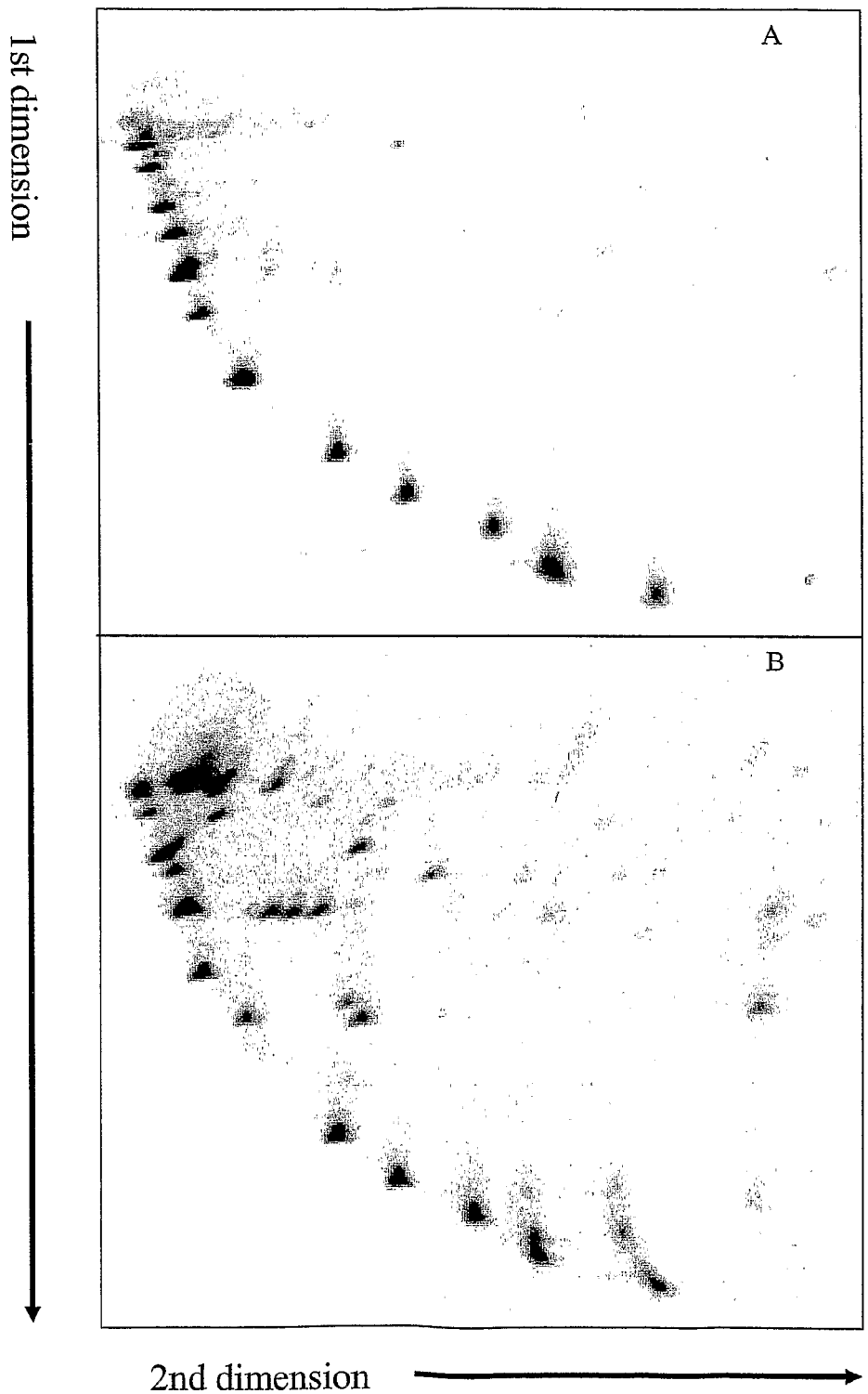

FIG. 10. Site-specific single-stranded breaks in a complex DNA sample assayed by 2D-SDE, conducted according to Example 5.

10A: Untreated BanI digested λ phage DNA labeled with Cy5.

10B: Identical DNA sample as in 10A treated with specific nicking endonuclease N.BstNBI to form site specific single-stranded breaks. After treatment with N.BstNBI, increased amount of DNA fragments migrated in front of the arc representing intact double-stranded DNA fragments, as shown in 10A.

Figure 11:
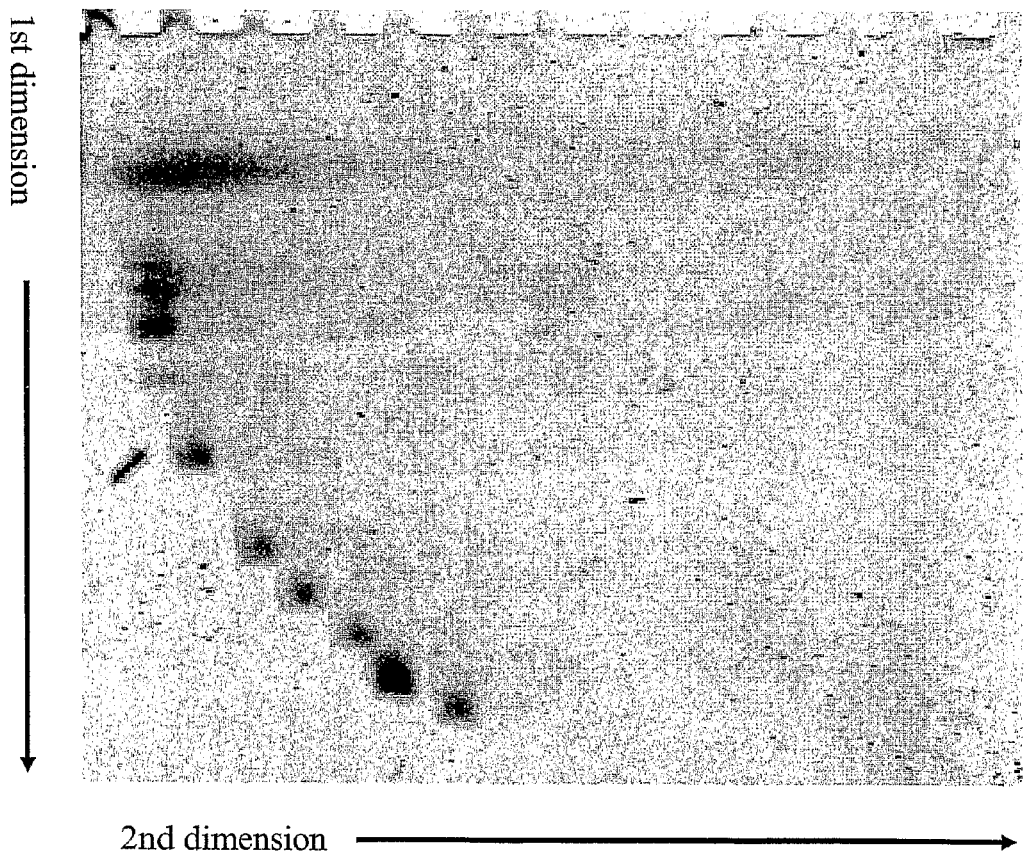

FIG. 11. Fluorescent image of 2D-SDE analysis to detect oxidatively induced single-stranded breaks in complex DNA sample, as described in Example 6. λ Phage DNA was exposed to $H_2O_2$ in a Fenton-like reaction and separated using 2D-SDE. As can been seen in the figure a widespread fluorescent signal was detected in front of the arc representing double-stranded DNA. This was due to non-specific formation of single-stranded breaks. Formation of fluorescent signal spots would be expected if single-stranded breaks were site-specific.

Figure 12:
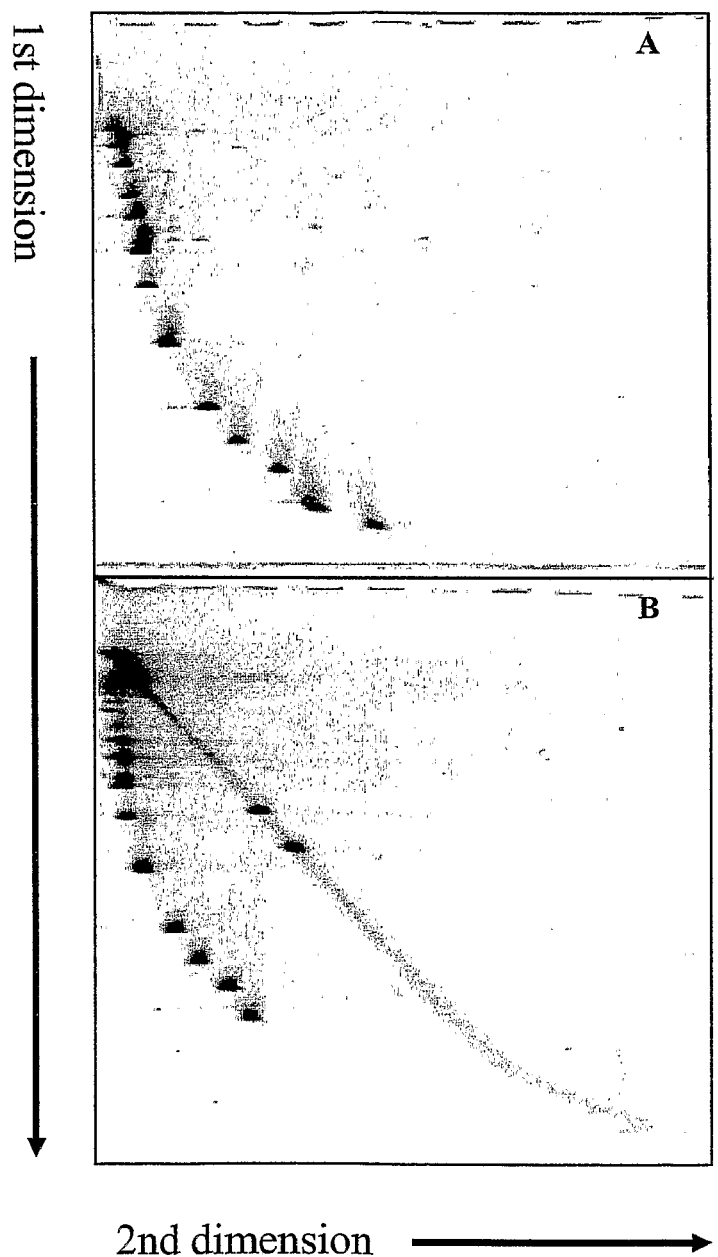

FIG. 12. Fluorescent image of 2D-SDE analysis to assay temperature-induced degradation of complex DNA sample, as described in Example 7.

12A: 2D-SDE separation of untreated Cy5-labeled BanI digested λ-phage DNA that was diluted in distilled water and kept at 4° C. for 20 hours. Several faint spots of DNA fragments could be detected, in front of the arc representing double-stranded sDNA fragments, indicating site-specific formation of single-stranded breaks.

12B: Identical DNA sample kept at 60° C. for 20 hours. Under such extreme conditions, at least three different changes in the DNA sample were detected: I) Non-specific formation of single-stranded breaks resulting in smearing of DNA in front of the arc representing double-stranded DNA fragments, II) increased amount of single-stranded DNA fragments of different length, resulting in a line of single-stranded fragments lying diagonally through the gel, and III) complete denaturation of the two shortest DNA fragments analysed, resulting in strong DNA spots lying inside the line of single-stranded fragments essentially vertically above their predicted place in the arc representing double-stranded DNA fragments.

Figure 13:
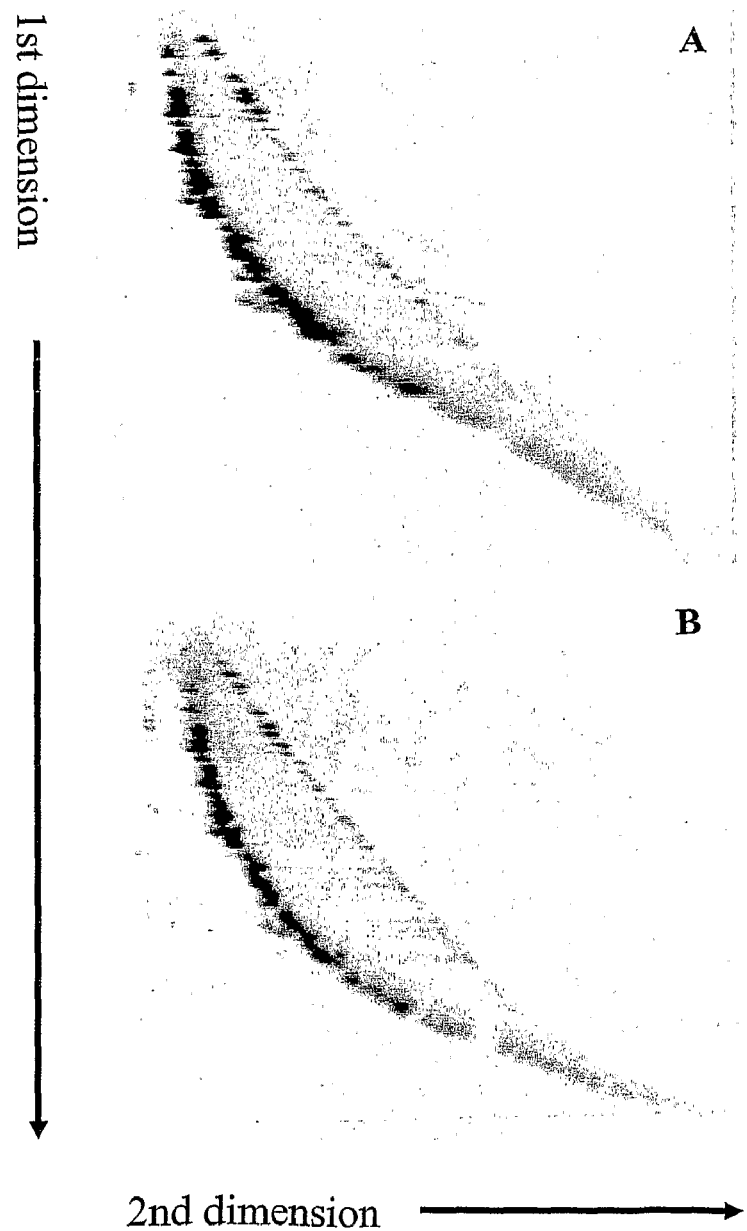

FIG. 13. Fluorescent image of 2D-SDE to assay time-induced degradation of a complex DNA sample, as described in Example 8. The second dimension electrophoresis was carried out at room temperature resulting in considerable renaturation of fragments (line in front of the arc representing the double-stranded DNA fraction) after the denaturation step.

13A: Analysis of freshly prepared λ phage DNA sample. Relatively few spots were detected in front of the arc representing double-stranded DNA fragments.

13B: Analysis of a six months old λ phage DNA sample. Increased amount of spots were detected in front of the arc representing double-stranded DNA fragments. This indicates site-specific degradation of DNA over long period of time.

Figure 14:
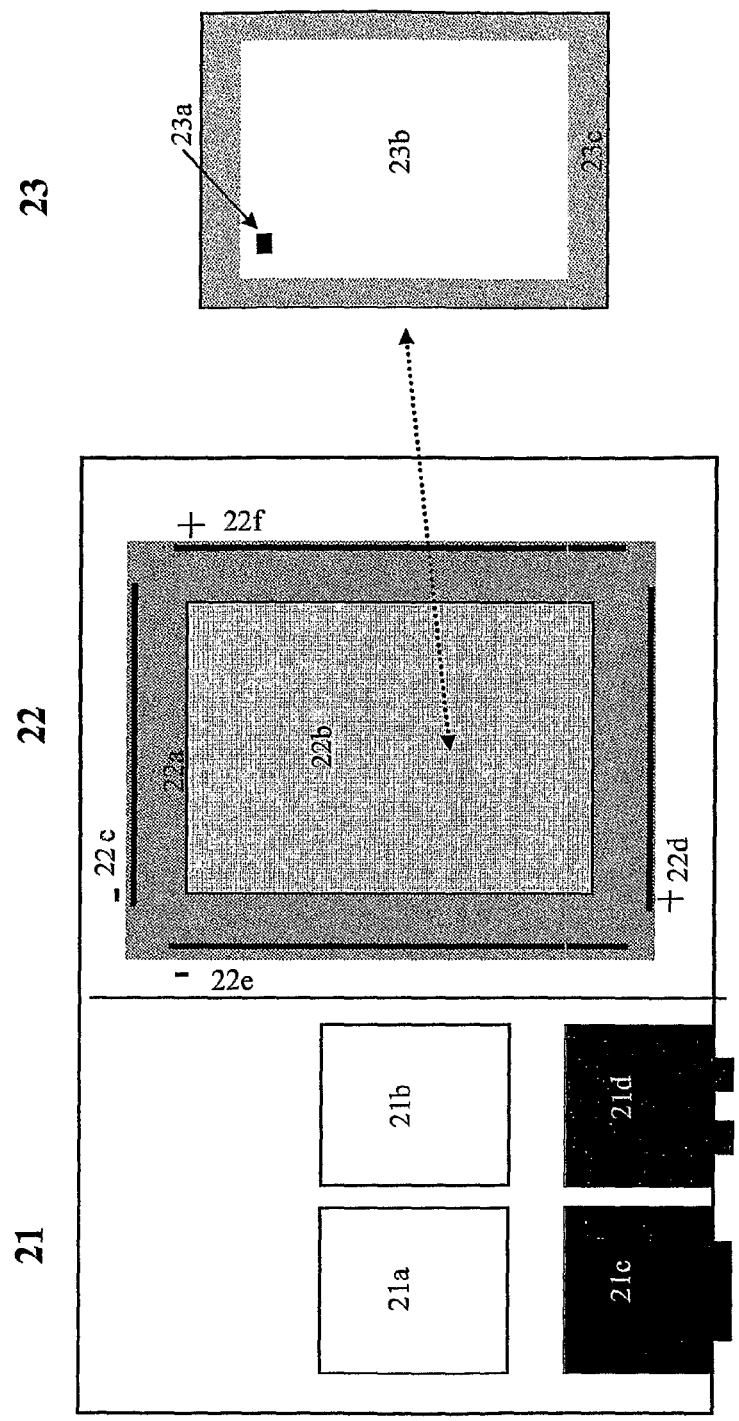

FIG. 14. A schematic drawing of a preferred electrophoresis system of the invention.

DETAILED DESCRIPTION OF THE INVENTION

The invention provides a method for separation and optionally isolation of single- and double-stranded nucleic acid fragments from a complex mixture of both. The invention can be used to screen nucleic acids preparations for their strandness with or without prior knowledge of their biological function or genome location. The invention can also be used to determine length distribution of single- and double-stranded nucleic acid fragments.

As can be inferred from the description herein, the invention can only be used for separation of linear, i.e. non-circular nucleic acids.

Nucleic acid samples suitable for analysis according to the present invention may comprise linear single- and/or double-stranded nucleic acid fragments of size range between 50 to 10,000 bp or nt but preferably in the range of about 100-1000 bp or nt. The source of nucleic acids may be prokaryotic, eukaryotic, viral, or synthetic. The source material may be genomic DNA, cDNA, RNA, DNA/RNA hybrids, PNA, LNA, plasmid DNA, or viral DNA or RNA including where the virus may be naturally occurring or serving as a vector for nucleic acids from a different source, or the lice. Depending upon the source of nucleic acids, they may have to be subjected to some purification, such as isolation from cellular sources, separation from proteins, removal of restriction enzyme and PCR inhibitors, etc. It should be emphasized that the method is particularly advantageous as it can be applied to complex DNA samples, i.e. samples containing large numbers of different nucleic acid fragments such as fragments of whole genomes or subsets thereof, and mixtures of genomic nucleic acids from more than one individual.

Depending on the desired objective of the invention for a given application the sample to be analysed can be from a single individual, a plurality of individuals, a genomic subset from one individual or the same genomic subset from a plurality of individuals, or a combined pool of a number of pools, wherein the nucleic acids may be treated in various ways before or after pooling samples and/or combining pools, e.g. cleaved, denatured, and renatured.

Nucleic acids of desired length can be provided, particularly in case of DNA, by restriction enzyme digestion, use of PCR or other in vitro amplification techniques, ligation, chemically or physically induced cleavage and the lice. Target nucleic acids may be labeled by isotopic or non-isotopic signals and they can contain a tag to allow specific capture after the separation. In some embodiments of the methods adaptors or linkers are ligated to the nucleic acid fragments.

In useful embodiments, the methods of the invention comprise estimating the length distribution within one or more of said single-stranded and double-stranded fractions after their separation. This is readily achieved by adding to the sample prior to electrophoresis an internal standard containing both single- and double-stranded nucleic acids of different known length that will show discrete spots in the gel after the electrophoresis with suitable staining. Preferably, such internal standards are pre-labeled with markers, e.g. fluorescent markers or the like.

After electrophoresis, the different fractions are preferably analysed to estimate the relative amount of single- and double-stranded nucleic acids in the sample as well as the length-distribution within each fraction. Such analysis is readily achieved by image analysis techniques and can be automated, as further described herein.

The present invention further provides a kit for determining strandness of complex nucleic acid samples using the methods of the present invention. The kit can contain premade 2D gels, which contain a denaturing agent suitable for the first dimension electrophoresis or means for preparing the 2D gel, including denaturing agent and gel chemicals. Further, the kit can contain a suitable buffer or buffer ingredients for both first and second dimension electrophoresis and optionally an agent to treat the gel before second dimension electrophoresis, to facilitate denaturation of all double-stranded molecules. The kit can additionally contain suitable adaptors for commercially available electrophoresis systems and heat resistant spacers, as the adaptors and spacers commonly supplied with presently available systems cannot withstand such high temperatures (e.g. in the range of about 75-95° C.) as maybe desired in the denaturing step of the present invention, between the first and second electrophoresis steps. The kit can further contain a specific heat-resistant closed container or a bag to put the gel sandwich in to eliminate evaporation during the denaturation step prior to second dimension. In useful embodiments, kits of the invention contain internal standards for both single- and double-stranded nucleic acid fragments to facilitate length analyzes and quantification of all strandness fractions. Such internal standards can be supplied a sample buffer solution to which the sample is added to be analysed, or in another suitable form to be mixed with the sample prior to electrophoresis. Further a detectable marker (e.g. a dye molecule) can by included to indicate when each electrophoresis step has reached completion.

Kits of the invention may further include a detecting agent including those that are mentioned herein, that binds to nucleic acid molecules in one or more of the separated fractions in the gel-matrix in order to make said nucleic acids detectable in the gel matrix after electrophoresis. Such detecting agent may be mixed with the sample prior to electrophoresis (such as in the case of, e.g. SYBR green dyes or Universal Linkage Systems (ULS)) or they may be supplied in a form to treat the gel after the electrophoresis.

Another aspect of the invention provides a system to perform the methods described herein. Such a system includes an electrophoresis cassette for supporting a gel sandwiched between supporting plates, the cassette can be configured such that gels are cast within the cassette; alternatively, precast gels are supplied with the system that fit in the cassette. In another embodiment, the cassette is supplied as a single-use unit with the gel prepared and inserted therein.

The system comprises an electrophoresis apparatus with a compartment for inserting the cassette. A sample port is located adjacent to or within the compartment in order to load a sample in the cassette to be analysed. In a preferred embodiment the compartment is configured such that the supplied cassette fits snugly therein and the electrophoresis is conducted essentially "dry", i.e. not in a buffer bath; this is possible by minimizing the size of the gel in which case a buffer is not needed as a supply of counter ions in order to accommodate the flow of electric current through the gel.

The apparatus further comprises two sets of electrodes, a first set of electrodes for the first dimension electrophoresis, and a second set of electrodes for the second dimension electrophoresis, the first set can sustain a first electrical field across the gel in an inserted cassette, when electrical power is applied to the electrodes, and the second set of electrodes can sustain a second electrical field across the gel essentially orthogonal to said first electrical field, when electrical power is applied to the electrodes. These electrical fields are interchangeable and applied separately as in conventional 2D electrophoresis. In a simpler version of the system a single set of electrodes can by used. In this case the cassette has to be rotated prior to the second dimension electrophoresis.

The system also comprises a controllable temperature system which is connected to a heating surface within said compartment to provide a pre-determined temperature to inside the gel matrix. By this arrangement and appropriate controlling means, the temperature of the gel can be controlled and adjusted substantially stepwise, such that the first dimension electrophoresis is run at a first temperature (e.g. 20° C.) after which the temperature of the gel is increased to a high temperature (e.g. 95° C.) for a limited period of time such as in the range of 1-5 min, in order to fully denature the double stranded nucleic acid molecules therein, subsequently the temperature is reduced (e.g. to 55° C.) for the second dimension electrophoresis to ensure that renaturation of denatured (single-stranded) nucleic acid molecules is eliminated.

The heating means can preferably comprise a thermoelectric device ("Peltier" device) with a heating surface in contact with one main surface of the cassette. In this case, said surface of the cassette should conduct the heat sufficiently to control the temperature within the gel itself.

The system preferably also comprises a power supply to provide adjustable power to the electrodes, it is particularly preferable that the system is provided with a computer to control operation of the system, i.e. which is connected to the power supply and heating means to control the applied voltages and currents (a first voltage to the first set of electrodes, a second voltage to the second set of electrodes), further to control the temperature of the heating device and thus control the operating temperature of the gel.

The computer is preferably loaded with computer software for the above controlling operations, which can preferably be configured such as to operate the system substantially automatically, i.e. supply suitable voltages and heating in a sequence of appropriately timed events to complete two-dimensional electrophoresis in accordance with the methods set forth herein.

It is an important feature of the present system that the apparatus and in particular the gel cassette should be able to withstand high temperatures, in the situations when the gel is heated for a brief period of time in between the first and second dimension electrophoresis. Preferably, the system is able to sustain and withstand operating temperatures within the gel of at least 75° C., more preferably of at least 85° C., and yet more preferably of at least 90° C. and more preferably of at least 95° C.

It will be particularly appreciated that the system of the invention can be miniaturized in order increase the speed of the duty cycle of the system. Microgels can be utilized having a size of less than about 10 $cm^2$, preferably less than about 5 $cm^2$, such as less than about 2.5 $cm^2$ e.g. about 0.5-2.5 $cm^2$, such as about 1 $cm^2$. Such microgels will require low sample volume but at the same time the detection limit for nucleic acids in the sample is lower. Further the temperature control in the system will allow high electric fields allowing fast separation of molecule in the gel.

Gels that are run with the methods described herein can be suitably analyzed with image analysis techniques. In one embodiment, the system of the invention comprises computer software loaded on a computer, for analysing such gel, based on a digitized image of said gel stained with a suitable detecting agent, the computer software comprising code such that when run by a computer, steps are performed to detect spots corresponding to internal standards, detect stained areas and determine boundaries of said areas, based on the location of the internal standards spots, assign detected areas as single-stranded or double-stranded nucleic acids, and estimate the density of detected areas to determine the ratio of single-stranded vs. double-stranded nucleic acids in the electrophoresed gel and preferably also the length distribution within each fraction.

A schematic illustration of a preferred system is shown in FIG. 14. The system is composed of two main parts. Firstly an electrophoresis unit that is further divided into a control part (21) and electrophoresis part (22). This electrophoresis unit contains a temperature-controlled compartment (22b) for a gel cassette (23) that is added prior to separation. The compartment (22b) is shown with an underlying heating plate, e.g. type Peltier thermoelectric heater. Two sets of electrodes are in the electrophoresis part allowing two-dimensional separation without rotating the gel cassette. The first set is shown as anode 1 (22c) and cathode 1 (22d), the second set as anode 2 (22e) and cathode 2 (22f). Around the gel cassette compartment is a buffer zone (22a) which is a conductive matrix or zone to be filled with buffer solution, which makes good contact with the gel and the electrodes to allow connection between the gel cassette and the electrodes.

The control unit contains a switch to change between electric field 1 and 2 (21b), unit to control the gel temperature (21a), connection (21c) to a computer (not shown) to allow software control of both 1a and 1b and a connection (21d) to power supply (not shown).

Secondly a gel cassette part is supplied (23). This cassette can either be used to cast a gel in or to fit a pre-casted gel. It is composed from two heat resistant plates in which the gel matrix is kept to ensure limited evaporation from the gel matrix (23b) At least one of the plates (facing the heating element) when the cassette is inserted should be heat-conducting in order to pass heat from the heating element to the gel. The cassette further comprises a sample loading slot (23a). Around the plates is a buffer connection zone (23c), a conductive matrix that will come in direct contact with the buffer zone of the electrophoresis unit allowing efficient current through the gel matrix under the applied electric field.

The invention provides in a further aspect a computer program product such as described above, loadable on a computer for analysing an image of a two-dimensional electrophoresis gel which has been run as described herein to determine the ratio of single-stranded (ss) and double-stranded (ds) nucleic acids in an analysed sample electrophoresed in the gel. The computer program product comprises program instruction means receive input values defining internal standards in said sample (their base pair length) comprising both single-stranded and double-stranded nucleic acids in differing known lengths; detect spots in said image corresponding to said internal standards, detect stained areas and determine boundaries of said areas, assign detected areas as single-stranded or double-stranded nucleic acids, and estimate density of detected areas to determine ratio of single-stranded vs. double-stranded nucleic acids in the electrophoresed gel. Further the boundaries of said areas can by compared to boundaries of the internal standards to estimate the length distribution of single- and double-stranded fractions.

Preferably, the internal standards are labelled to produce another detectable color than the color of the stained sample nucleic acids, thus the image detection software can be set to identify a specific wavelength band for identifying the standard spots. After the internal standards spots have been assigned x-y coordinates in the 2D image space, functions are derived defining the relationship between location of the spots (typically the y-coordinates), and the basepair length of the standards in each spot.

The sample spots/areas are detected by reading from the image the appropriate color wavelength corresponding to the detection agent (label/stain) being used, the boundaries of said spots/areas are determined and the areas assigned as ss or ds nucleic acids according to their location compared to the internal standards. The boundaries are determined by conventional methods known in the art, e.g. applying black top-hat transform to the image, or the like. In order to estimate the density of the detected areas, a background value is determined and subtracted from the measured intensities of the pixels within the areas. The areas can then be integrated in order to quantify the ratio between single-stranded and double-stranded nucleic acids. Note that under certain conditions, as described above, the method can further be sued to separate DNA:DNA duplexes from hybrid duplexes (DNA: RNA) which will show up as a third region in the gel and can be analysed and quantified as described above, preferably by using appropriate standards for such hybrid molecules.

In a first major aspect of the invention, a method is provided for both strandness- and length-dependent separation of non-circular nucleic acids fragments (i.e. separation of single-stranded from double-stranded nucleic acid fragments and separation according to length within each group), comprising: providing a sample of nucleic acid fragments comprising any of the above source nucleic acids that may be prepared as described above; loading the sample in a gel electrophoresis apparatus and electrophoresing in a first dimension said sample through a gel-matrix under a first set of pre-determined electrophoresis conditions such that double-stranded nucleic acid fragments remain intact; and then conditions are altered prior to the second dimension electrophoresis such that complete denaturation (strand separation) of double-stranded fragments is achieved; subsequently electrophoresing said gel in a second dimension under a second set of electrophoresis conditions that prevent the re-annealing of double strands. Essentially, the first dimension electrophoresis allows separation of the sample nucleic acid fragments based on strandness and length, and the second dimension electrophoresis allows separation of the sample fragments based only on their length; difference of said conditions is established with a chemical and/or a physical agent which is capable of eliminating the strandness-based migration difference between the nucleic acid fragments.

Polyacrylamide gels useful in the method of present invention may contain a wide percentage range of polyacrylamide that can be suitably selected according to the estimated size distribution of sample nucleic acids fragments. Typically, gels in the range of about 2% to about 20% polyacrylamide are used, preferably in the range of about 5% to about 15% polyacrylamide. The size of the gel and electrical conditions during the electrophoresis (voltage, current, electrolyte concentration, etc.) can be adjusted according to the degree of migration necessary to maximize separation of nucleic acid fragments to be analysed. Other gel-matrixes than polyacrylamide may also be used to carry out 2D-SDE including polyacrylamide derivatives such as MDE, and LongRanger™.

Buffer systems for either of the dimension can be chosen according to the gel-matrix used in each specific embodiment of the method of invention. The same buffer system is not necessarily used in both dimensions.

Typically the gel-matrix used in the present invention contains a denaturating agent in a concentration that does not cause denaturation (strand separation) of double-stranded nucleic acid fragments but reduces secondary structures of both single- and double-stranded nucleic acid fragments.

In certain embodiments of the method, no denaturating agent is added to the gel-matrix prior to the first dimension of separation. In these embodiments the gel may be incubated in a buffer containing one or more denaturating agent of choice before the second dimension electrophoresis where complete denaturation of double-stranded fragments is required.

The denaturing agent that may be incorporated in the gel-matrix prior the first dimension electrophoresis is preferably one or more of an aliphatic alcohol such as methyl, ethyl, isopropyl, n-propyl, allyl, butyl, isobutyl, and amyl alcohols and ethylene glycol; cyclic alcohols such as cyclohexyl, benzyl, phenol, and p-methoxyphenol alcohol and inositol; alicyclic compounds such as aniline, pyridine, purine, 1,4-dioxane, butyrolactone, and aminotriazole; amides such as formamide, ethylformamide, dimethylformamide, acetamide, N-ethylacetamide, N,N-dimethylacetamide, propionamide, glycolamide, thioacetamide, valerolactam; urea compounds such as carbohydrazide, 1,3-dimethylurea, ethylurea, t-butylurea, thiourea, and allylithiourea; carbamates such as urethan, N-methylurethan and N-propylurethan; detergents including Tween 40 and Triton X-100, and other compounds such as cyanoguanidine, sulfamide, glycine, acetonitrile, and DMSO. In the cases where the gel is soaked in a denaturing agent after the first dimension but prior to the second dimension electrophoresis one or more of the above agents may be used.

Other chemical agents and physical factors that can be used in the present invention to reduce differences in strandness may be identified or developed by those skilled in the art. The concentration of said chemical agent used in the method of invention is dependent on its nucleic acid binding affinity, denaturating capacity, ability to reduce strandness difference and secondary structures, and stability of the agent in the gel-matrix or the buffer.

In a particularly useful embodiment of the method the denaturating agent, urea is added to the gel-matrix prior to the first dimension electrophoresis. Here, urea acts in three different ways: I) to reduce the differences in migration due to conformation but not strandness of all nucleic acid fragments (both single- and double-stranded) in the first dimension, II) to facilitate the complete temperate-induced denaturation (strand separation) prior to the second dimension, and III) to ensure that renaturation (reannealing) does not occur before or during the second dimension electrophoresis.

The first gel electrophoresis step can be carried out at widely different temperatures but in a typical application the temperature is in the range between 5° C. to 50° C. In typical practice of the method of invention, a mixture of single- and double-stranded nucleic acid fragments is separated at room temperature.

After the first dimension electrophoresis, which allows both separation according to length and strandness of the nucleic acid fragments as discussed above, the gel is typically removed from the electrophoresis apparatus, however with appropriate design of an apparatus such as is further described herein removing the gel is not necessary. The gel is incubated at a high temperature to cause total denaturation of all nucleic acid fragments. During the incubation the gel is partially or fully enclosed (e.g. kept between plates) to limit evaporation from it. The gel is incubated for a period of time, which can vary depending on the size, matrix type and thickness of the gel used in the embodiment of the method. In other embodiment of the methods the double-stranded nucleic acids are denatured with a chemical agent or mixture of physical and chemical agents.

The conditions in the second dimension electrophoresis step are different from those of the first dimension, e.g. by altering a physical parameter or chemical agent, such as temperature or concentration of urea, which will further affect the strandness of the sample nucleic acid fragments.

After the physical and/or chemical-induced denaturation for a given amount of time the gel is arranged in a suitable electrophoresis device for the second dimension electrophoresis. All nucleic acid fragments now have the same strandness (i.e. they are all single-stranded). Therefore all nucleic acid fragments in the gel separate according to their length. Consequently, fragments of different length that overlap after the first dimension due to difference in strandness will be resolved in the second dimension. Because the nucleic acid fragments that were originally single-stranded have essentially the same migration velocity in both dimensions they form an approximately diagonal line in the gel. Nucleic acid fragments that were double-stranded during the first dimension but single-stranded during the second dimension form an arc, as these fragments migrate relatively faster in the first dimension than in the second dimension. Therefore a strandness- and length-dependent separation of single- and double-stranded nucleic acid fragments is obtained by the method of the present invention.

Single-stranded nucleic acids fragments migrate relatively slower than their double-stranded counterparts. The diagonal line of the single-stranded fragments is therefore displaced in front of (on the right-hand side of in the figures) the arc representing the double-stranded nucleic acid fragments. If two nucleic acid fragments identical in length, one single-stranded, and the other double-stranded are separated in the system, the single-stranded fragment should be located vertically above the double-stranded fragment.

Nucleic acids fragments in the gel can be readily detected using standard biochemical techniques. They include well-known methods such as staining of the gel with fluorescent nucleic acid stains, like ethidium bromide (EtBr) and SYBR® green I or II, using detection systems familiar to those skilled in the art. Nucleic acid fragments can also be detected using isotopic or non-isotopic pre-labeled nucleic acid fragments and detection systems such as films, phosphor- and fluoroimagers, or similar methods familiar to those skilled in the art.

Isolation of nucleic acids from the gel after the 2D-SDE separation may be done using well-known methods such as elution from gel pieces and electro-elution. Nucleic acid fragments may in some embodiments of the methods contain adaptors for e.g. PCR amplification after isolation from the gel-matrix.

In accordance with the first major aspect of the invention described above the methods of the invention can be used in different embodiments.

In the particular embodiments described in Examples 1 and 2, 2D-SDE is used to separate ssDNA and dsDNA fragments both in a strandness- and length-dependent manner. In typical embodiments of this kind, the sample to be analysed comprises genomic samples or pool of samples that have been prepared in such way that the length distribution of fragments are between 50-10,000 bp. The sample is then analysed using the method described above. Following the 2D-SDE separation the diagonal line representing the single-stranded DNA fragments and the arc representing the originally double-stranded DNA fragments can be quantified and/or isolated.

As is illustrated with a particular embodiment in Example 3 below the method of the invention can be used for separation of bulge-containing DNA fragments from perfectly matched DNA fragments. Bulge-containing DNA fragments have lower migration velocity compared to their perfectly matched counterparts when double-stranded DNA is separated in PAGE gel with or without 7 M urea. When the same fragments are separated in their single-stranded form they all migrate essentially according to their length, especially in gels containing urea. Therefore, heteroduplexes containing bulges can be separated from perfectly matched DNA fragments, using 2D-SDE, in such way that the bulge-containing fragments are located in front of the arc representing double-stranded perfectly matched DNA fragments after the separation.

As illustrated with a particular embodiment in Example 4 below the method is powerful for estimation of renaturation efficiency and calculation of the renaturing kinetics of complex DNA samples. In a typical embodiment of this kind, the sample to be analysed comprises genomic samples or pool of samples that have been cleaved, denatured and renatured (reannealed). The sample is than analysed using the method described above in accordance with the first major aspect of the invention. Following the separation the diagonal line representing the single-stranded DNA fragments and the arc representing the originally double-stranded DNA fragments are quantified, e.g. using a fluoro-imager.

As is illustrated with a particular embodiment in Example 5 below, the method of the invention can be used to estimate the quality of PCR products and product resulting from other in vitro amplification methods. In a typical embodiment of this kind the sample analysed comprises PCR products amplified from different kinds of genomic material or cDNA. The complexity of the PCR products may vary according to the PCR method used from being one to several hundred thousands different fragments. After the PCR reaction, the products are separated using the method of invention. Single-stranded and double-stranded PCR products can be quantified and length distribution of both fractions measured. In a particularly useful embodiment the quality of PCR amplified genomic representations are estimated. The term "genomic representation" as used herein relates to a subset of a genome comprising genetic material of interest. Creation of genomic representations is therefore one way to reduce the complexity of the target genome. Methods for creating genomic representations have been described in previous publications by one of the present inventors, see in particular in WO 00/24935, and also by Lucito et al. in the book DNA microarray (Bowtell and Sambrook 2003).

Yet a further aspect of the invention is illustrated with a particular embodiment in Example 6. The method of the invention is used to reveal the composition of uncharacterized nucleic acid samples. Such nucleic acid samples may be isolated from various biological sources. One useful embodiment is to characterize nucleic acids isolated from human plasma. Isolation of free nucleic acids from plasma can be performed using standard methods known to persons skilled in the art. In this way it is possible to reveal the composition of the nucleic acid in the sample with regard to their strandness and also to estimate the length distribution of both single- and double-stranded nucleic acid fragments.

As is illustrated in Example 7, one useful embodiment of the method enables measurement of the efficiency of cDNA synthesis. In a typical embodiment of this kind an isolated mRNA is subjected to a first strand cDNA synthesis followed by a second strand synthesis using methods known to those skilled in the art. After both the first and the second strand synthesis, the method of the invention can be used to separate single- and double-stranded cDNA fragments. Further, the method allows identification of RNA:DNA hybrids in the mixture. Such hybrids are an intermediate product formed after the first strand synthesis. RNA:DNA hybrids form A-form lice double-stranded helices which are shorter per base-pair than the corresponding B-form typically adopted by dsDNA helices. Therefore the method measures efficiency of both first and second strand formation and length distribution of all three fractions, i.e. single-stranded DNA, double-stranded DNA, and RNA:DNA hybrids. This analysis also allows estimation of labelling of cDNA molecules.

In another aspect of the invention a method is provided to normalize nucleic acid samples. Genes are expressed at various levels in each cell. Differences in amplification efficiency of various mRNA can also result different leaves of cDNA molecules when creating amplified cDNA libraries. For many different types of analysis of amplified cDNA libraries it is important to have uniform abundance of all products in the samples. Methods for normalization are based on the fact that renaturation cDNA follows second-order kinetics and depends strongly on the concentration of each fragment. Therefore rare gene products renature less rapidly than the highly concentrated abundant products. During renaturation the remaining single-stranded fraction therefore becomes progressively more normalized, i.e. the concentration of individual cDNA fragments becomes more even. One can obtain a normalized sample by isolating the single-stranded fraction remaining after partial renaturation. Currently the major bottle-neck in such an approach is an efficient separation between single- and double-stranded products. The standard technology is to use differential binding of single- and double-stranded DNA fragments to hydroxyaptite columns. This technique is cumbersome and does not discriminate fully between single-stranded and partially double-stranded DNA fragments. Using the method of invention for physical separation of single- and double-stranded nucleic acid fragments followed by direct isolation of the pure single-stranded nucleic acid fraction from the gel-matrix e.g. by electroelution may greatly facilitate normalization of nucleic acid samples.

In a second major aspect of the invention, a method is provided to separate nucleic acids fragments containing single-stranded breaks (including nicks) from intact double-stranded nucleic acid fragments. The same experimental setup is used as described above relating to the first aspect of the invention. During the first dimension electrophoresis double-stranded nucleic acid fragments containing one or more single-stranded breaks have essentially the same migration velocity as their intact double-stranded counterparts.

After the first dimension electrophoresis, where all double-stranded DNA fragments (with or without single-stranded breaks) migrate essentially according to their length, all nucleic acid fragments are denatured in the gel-matrix as described above. This ensures complete denaturation (strand separation) of all nucleic acid fragments in the gel. Intact double-stranded nucleic acid fragments give rise to two equally long single-stranded fragments that are complementary. A double-stranded nucleic acid that contains e.g. one single-stranded break (or nick) is results in three single-stranded fragments after denaturation (strand separation). One is of the same length as the original double-stranded fragment representing the intact strand and the other two are shorter. The two shorter fragments are complementary to the long fragment and they represent the break containing strand.

After temperature- or chemical-induced denaturation the gel is arranged for the second-dimension electrophoresis. All nucleic acid fragments now have the same strandness (i.e. they are all single-stranded). Therefore all nucleic acid fragments in the gel separate based on their original length except DNA strands containing nicks or breaks in the original double-stranded fragments. They now have higher migration velocity consistent with their shorter length. Therefore the nucleic acid fragments that contained single-stranded breaks or nicks show unique migration velocity in the second-dimension. Such single-stranded fragments migrate in front of the arc representing intact double-stranded nucleic acid fragments.

As described herein, the method according to this aspect of the invention can readily be applied to separate intact double-stranded nucleic acid fragments from those containing single-stranded breaks or nicks. Single-stranded breaks in double-stranded nucleic acid fragments are induced in various ways, including: oxidation, ionization radiation, incomplete replication, UVA-radiation, incomplete ligation in recombinant DNA, increased temperature, alkaline or acid buffer conditions, activity of sequence specific nicking enzymes, activity of endonucleases, lyases, glycosylases, ribonucleases, or other enzymes which detect specific lesions, bulges, or mismatches in the genome, and activity of synthetic or natural occurring chemical compounds e.g. osmium, hydroxylamine, potassium permanganate, tetraethylammoninum chloride, and rhodium(III) complexes and the like.

As is illustrated with the particular embodiments in Example 8, 9, 10, and 11, this aspect of the invention can be used to detect single-stranded breaks in complex DNA samples induced by different chemical or physical factors.

Another important embodiment of the invention provides a method to rapidly scan for mutations or polymorphisms in complex samples. Prior to the screening the sample is denatured and renatured and sometimes control fragments are then added. The sample is then treated with enzymes or chemical that generate site-specific single-stranded breaks where mutations or polymorphisms are located that form mismatches in heteroduplexes. At least two endonucleases (endonuclease V and CEL I) have been reported to cleave all 8 different single-base pair mismatches and smaller insertion/deletion bulges in heteroduplexes (Yao and Kow 1994; Oleykowski, Bronson Mullins et al. 1998). Often such methods suffer from background signal due to non-specific cleavage. Recently it was reported that a thermostable DNA ligase may reduce the non-specific cleavage by resealing the background nicks (Huang, Kirk .et al. 2002). A particular, useful embodiment combines cleavage detection with enzymes or chemicals and the methods described above. The result is a powerful method to potentially detect all DNA variations simultaneously in complex samples of multiple fragments. This method would greatly increase the throughput of enzymatic and chemical cleavage methods and therefore reduce cost of analysis. This special embodiment is called Two-dimensional Nick-Dependent Electrophoresis (2D-NDE). 2D-NDE should not be as strongly dependent on physical properties of each amplicon as e.g. two-dimensional gel scanning (TDGS). For instance, amplicons do not need to contain only one melting domain. Therefore, generation of multiple amplicons maybe achieved with diverse approaches known to those skilled in the art.

Other similar embodiments are introduced by combing the method of the invention with other enzymes that detect and cleave various lesions in DNA e.g. UV-lesions.

The methods used with and the utility of the present invention can be shown by the following non-limiting examples and accompanying figures.

EXAMPLES

Example 1

2D-SDE for Length-independent Separation of a Complex Sample Containing Cy3-labeled Single-stranded DNA Fragments and Cy5-labeled Double-stranded DNA Fragments Derived from λ Phage DNA λ Phage DNA was digested with the restriction enzyme NdeII resulting in formation of 116 different fragments ranging in size between 12 to 2225 bp. After the digestion the sample was divided into two aliquots. One aliquot was labelled by extension of overhangs using Klenow fragment and Cy5-dCTP. The other aliquot was labelled in the same way with Cy3-dCTP. After labelling reactions the products were purified using GFX PCR and Gel band purification kit.

Fraction of both Cy3- and Cy5-labelled DNA samples were denatured at 95° C. for 5 min followed by quick transfer to ice-water slush to form single-stranded DNA fragments. Three pools of samples were prepared containing equal amount of Cy3- and Cy5-labelled DNA. The first pool contained denatured Cy3-labelled DNA and untreated Cy5-labeled DNA. The second contained denatured Cy3- and Cy5-labeled DNA fragments. The third contained untreated Cy3- and Cy5-labeled DNA fragments.

These three pools of samples were independently separated by 2D-SDE. The gel-matrix consisted of 10% polyacrylamide prepared from 29:1 acrylamide: bisacrylamide mixture and 7 M urea. The gel was polymerized in 1×TBE buffer (89 mM Tris base, 89 mM borate, and 2 mM EDTA). The first dimension electrophoresis was done in BioRad Mini Protean II vertical electrophoresis system. The gel was run at room temperature (RT) for 1 hour at a constant 20 mA in 1×TBE buffer.

After first dimension electrophoresis the gel sandwich was placed on a heat-block (dri-block Techne) and incubated at 92° C. for 3 min. To ensure better heat distribution, one of the 92° C. hot aluminum cubes was placed on top of the gel sandwich. After the denaturation the gel sandwich was cooled to RT.

Second dimension gel electrophoresis was done in a Pharmacia Multiphor horizontal electrophoresis system. The gel was run at RT, perpendicular to the first dimension electrophoresis using 1×TBE buffer for 1 hour at constant power of 5 W. Connection between electrodes in buffer chambers and gel-matrix was achieved with paper electrode wicks.

Fluorescent detection of DNA fragments was carried out using fluorescence-scanning mode of the AP Biotech's Typhoon 8600 variable mode imager, with excitation wavelength 633 nm and the 670BP30 emission filter for Cy5 detection and excitation wavelength 532 nm and the 580BP30 emission filter for Cy3 detection.

Figure 1:
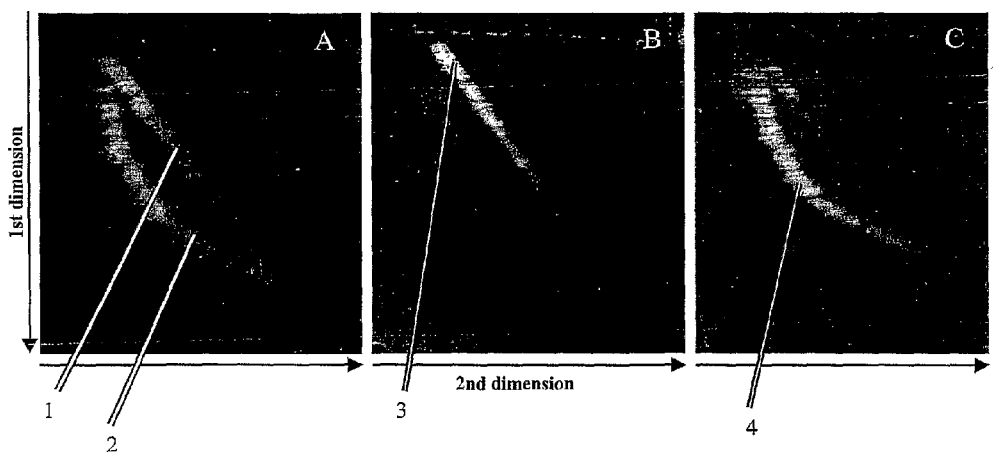
FIG. 1. Fluorescent images of 2D-SDE analyses from Example 1. The 2D-SDE system was used to separate single- and double-stranded DNA fragments representing the λ phage genome.

As shown in FIG. 1A, single-strand DNA fragments formed a line lying diagonal through the gel (red), double-stranded DNA fragments formed an arc lying left to the line of single-stranded fragments (green). 2D-SDE of pools of denatured Cy5- and Cy3-DNA fragments (FIG. 1B) and untreated Cy5- and Cy3-DNA fragments (FIG. 1C) resulted in co-migration of Cy5 and Cy3 labelled fragments (yellow line or arc, respectively). If all DNA fragments were denatured the line was comparable to the red line in FIG. 1A. If all DNA fragments were untreated the yellow arc was comparable to the green arc in FIG. 1A.

Example 2

2D-SDE for Strandness and Length-dependent Separation of a Complex Sample Containing Cy3-labeled Single-stranded DNA Fragments and CY5-labeled Double-stranded DNA Fragments Derived from Human Genomic DNA To further examine the capacity of 2D-SDE, corresponding experiments as described in Example 1 were performed, now using Cy5- and Cy3-labeled NdeII digested human DNA. Genomic DNA was isolated from whole blood (Puregene DNA isolation kit, Gentra Systems).

Similar results were obtained as for the λ phage DNA in Example 1. As shown in FIG. 2A, all single-stranded DNA fragments form a line lying diagonal through the gel (red). Double-stranded DNA fragments form an arc lying left to the line of single-stranded fragments (green). No separation of DNA bands was obtained due to the great number and length heterogeneity of digested human DNA. Separation of pools containing denatured Cy5- and Cy3-DNA fragments FIG. 2B) and untreated Cy5- and Cy3-DNA fragments (FIG. 2C) resulted in co-migration (yellow line or arc respectively). If all DNA fragments were denatured the line was comparable to the red line in FIG. 2A. If all DNA fragments were untreated the yellow arc was comparable to the green arc in FIG. 2A.

Example 3

2D-SDE to Reveal the Presence of Bulge-containing DNA Fragments in a Complex DNA Sample A 274 bp DNA fragment was amplified from exon 11 in the C-kit gene from an individual known to be heterozygote for a 9 bp deletion mutation in that exon. Such amplification resulted in four different DNA hybrids. Two homohybrids (265 bp and 274 bp) and two 265 bp heterohybrids each were containing 9 base bulge in either the sense or anti-sense strand. The PCR products were purified using GFX PCR and Gel band purification kit.

GeneRuler™ 100 bp DNA Ladder Plus (14 fragments ranging from 100 to 3000 bp) was labelled with T4 DNA polymerase (Fermentas). The ladder was first treated with T4 DNA polymerase without dNTP's. Under these conditions the enzyme has strong 3' to 5' exonuclease activity. Mixture of Cy5-dCTP and unlabeled dATP, dTTP and dGTP was then added to the reaction allowing the enzyme to have strong polymerase activity. The ladder was then purified using GFX PCR and Gel band purification kit.

The PCR products and the Cy5 labelled DNA ladder were pooled and separated with 2D-SDE using the same conditions and setup as described in Example 1, except the second dimension electrophoresis was performed at 55° C.

After 2D-SDE separation, the gel was stained with Ethidium Bromide (EtBr) (1 µg/ml) in 50 ml of 1×TBE. Fluorescent detection of EtBr stained or Cy5 labelled DNA fragments was carried out with AP Biotech's Typhoon 8600 variable mode imager. As is shown in FIG. 3, perfectly matched DNA fragments formed an arc. The two DNA fragments containing bulges migrate in front of the arc of perfectly matched DNA and were aligned in the second dimension (i.e. vertically) to their perfectly matched counterparts.

Example 4

2D-SDE for Estimation of Renaturation Efficiency and Calculation of Renaturation Kinetics of λ Phase DNA.

λ Phage DNA (10 µg) was digested for 60 min with 30 U of BanI (Amersham Biosciences) at 50° C. This creates a sample of intermediate complexity (26 DNA fragments ranging in size from 6 to 18362 bp). The digested DNA was then labelled with Cy5 as described in example 1.

Ten identical samples of BanI digested and Cy5-labeled λ phage DNA (114 ng in 10 µl of 0.3×SSC) were denatured at 95° C. for 5 min. The temperature was then decreased to 68° C. at maximum rate. Samples were directly transferred to ice-water slush at time points of 0, 1, 2, 5, 15, 30, 60, 120, 180, and 1440 min.

Each sample was separated using 2D-SDE in 8% PAGE containing 7 M Urea for 45 min in the first dimension and at 55° C. for 60 min in the second dimension. Otherwise the same setup was used as described in Example 1. Examples of separation at several time points are given in FIG. 4.

After electrophoresis all gels were scanned for Cy5 fluorescence as described in Example 1. We measured fluorescent density of the arcs representing single-stranded DNA and double-stranded DNA for all time points using ImageQuant 5.1 (Amersham Biosciences). From this data we calculated the fraction of single-stranded DNA for each time point and plotted 1/fraction single-stranded DNA vs. time (FIG. 5). The plot should give a linear relationship if the data reflects ideal second order kinetics with the slope of the line representing the apparent second order rate constant k. From the best line equation $t_{1/2}$ was calculated to be 7110 seconds, and $C_0t_{1/2}$ to be 0.24 Ms. A $C_0t$ curve was also plotted for the reaction and compared to the ideal second order $C_0t$ curve (FIG. 6).

Example 5

2D-SDE to Estimate Quality of Complex PCR Reactions

DNA sample isolated from whole blood was digested with BstYI and purified. Adaptors were ligated to the restriction fragments. Complex PCR using adaptor specific primer and Alu 3' specific primer with internal BbsI site was performed as described in further detail in WO 00/24935 which is fully incorporated herein by reference. The resulting Alu 3' fragments were purified using GFX™ columns. The estimated number of different fragments in this complex PCR is in the order of $1-3\times10^5$.

Fractions of the complex PCR reactions were separated with 2D-SDE using same conditions as in Example 3. After the separation the gel was stained with EtBr and fluorescent scanned as described in example 3 A considerable fraction of the PCR products was single-stranded, demonstrating efficiency of amplification (FIG. 7).

Example 6

2D-SDE to Reveal the Composition of an Uncharacterized DNA Sample

Free nucleic acids from plasma of a healthy adult were isolated with the High Pure Viral Nucleic Acid Kit (Roche). Manufacturer's protocol was followed but with five-fold volume of all reagents. After isolation, the uncharacterized DNA sample was concentrated using SpeedVac. The concentrated DNA sample (23 ng/ml) was separated using 2D-SDE as described in Example 1. After 2D-SDE separation, the gel was stained with EtBr and scanned as described in Example 3. 2D-SDE revealed that this uncharacterized nucleic acid sample from plasma contained both single- and double-stranded DNA fragments of various lengths (FIG. 8).

Example 7

2D-SDE to Estimate the Efficiency of cDNA First Strand Synthesis

High Range RNA ladder (200 to 6000 nt) was purchased from Fermentas. The ladder was subjected to first strand cDNA synthesis using the RevertAid H Minus First Strand cDNA Synthesis Kit (Fermentas) where cDNA synthesis was primed with the included random hexamers. Cy5-dCTP was added into the reaction mixture to label the synthesized cDNA strand. Samples taken after the first strand synthesis reaction were mixed with 100 bp double-stranded DNA ladder (Fermentas) and separated using the 2D-SDE. The same conditions and setup as described in Example 3. 2D-SDE revealed that the mixture contained large amount of RNA: DNA hybrids as expected (FIG. 9). A specific arc representing the RNA:DNA hybrids is formed (green). The arc representing dsDNA (red) is in front of the RNA:DNA arc.

Example 8

2D-SDE to Detect Site-specific Single-stranded Breaks in Complex DNA Samples

We assumed that after denaturation in the 2D-SDE system, double-stranded DNA fragments containing nicks or single-stranded breaks in the phosphodiester DNA backbone would give rise to single-stranded DNA fragments shorter than the original double-stranded DNA fragments. Such single-stranded DNA fragments will migrate in front of the arc representing intact double-stranded DNA fragments. To test if it is possible to use 2D-SDE as a tool for detection and quantification of single-strand breaks in complex DNA samples the following experiment was performed.

λ Phage DNA was digested with BanI and labelled with Cy5 as described in example 4. Cy5-labelled BanI digested λ phage DNA (500 ng) was then incubated in 50 µl of 1×NEB-uffer N.BstNB I with 10 U of nicking endonucleases N.BstNB I (New England Biolabs) for 60 min at 55° C. to generate site-specific single-stranded breaks. DNA was purified from the reaction mixture using GFX purification kit.

N.BstNB I treated DNA and untreated control DNA were separated using 2D-SDE using the same conditions and setup as described in Example 3.

A considerable quantity of DNA bands lying in front of the arc representing the double-stranded DNA fractions was detected if the DNA is treated with the specific nicking endonuclease (FIG. 10).

Example 9

2D-SDE to Detect Oxidatively Induced Single-stranded Breaks in Complex DNA Samples Cy5 labelled λ Phage DNA (prepared as described in Example 4) was exposed to $H_2O_2$ in a Fenton-like reaction to form non-specific single-stranded breaks. λ phage DNA (228 ng) was incubated in 20 µl of 0.2 mM $H_2O_2$ (Merck) and 0.4 mM $CuSO_4$ (Merck) for 0, 1, 5, 10, 20, and 30 min. Subsequently the reactions were quenched by adding 1 µl of 0.5 M EDTA (Sigma).

As an example DNA fragments treated for 5 min with $H_2O_2$ and untreated control DNA fragments were separated with 2D-SDE using the same conditions and setup as described in Example 3. A widespread fluorescent signal was detected in front of the arc representing double-stranded DNA fragments, but no strong signal spots. This indicated random formation of single-stranded breaks (FIG. 11).

Example 10

2D-SDE to Assay Temperature-induced Degradation in Complex DNA Samples

λ Phage DNA was digested with BanI and labelled with Cy5 as described in Example 4. Cy5-labelled BanI digested λ phage DNA (228 ng) was incubated in 20 µl of water for 20 hours at either 4° C. or 60° C.

These two DNA samples were separated using 2D-SDE using the same conditions and setup as described in Example 3. The 2D-SDE separation revealed that these extreme conditions induced non-specific single-strand breaks, single-strandness of DNA fragments, and total denaturation of the two the smallest double-stranded DNA fragments (FIG. 12).

Example 11

2D-SDE to Assay DNA Degradation During Long-term Storage of Complex DNA Samples

λ Phage DNA was digested with the restriction enzyme NdeII, labelled with Cy5 and purified as described in example 1. The sample was kept at 4° C. for six months in 1×TE buffer. An identical fresh DNA sample was prepared six month later and these two samples separated using 2D-SDE as described in Example 1.

The 2D-SDE separation revealed that the long-term storage of linear DNA fragments induced site-specific single-strand breaks as can be judged by increased density of DNA bands lying in front of the arc of intact dsDNA fragments (FIG. 13).

References

Bowtell, D. and J. Sambrook (2003). *DNA microarrays: a molecular cloning manual*. Cold Spring Harbor, N.Y., Cold Spring Harbor Laboratory Press.

Huang, J., B. Kirk, et al. (2002). "An endonuclease/ligase based mutation scanning method especially suited for analysis of neoplastic tissue." *Oncogene* 21(12): 1909-21.

Kovar, H., G. Jug, et al. (1991). "Two dimensional single-strand conformation polymorphism analysis: a useful tool for the detection of mutations in long DNA fragments." *Nucleic Acids Res* 19(13): 3507-10.

McMaster, G. K. and G. G. Carmichael (1977). "Analysis of single- and double-stranded nucleic acids on polyacrylamide and agarose gels by using glyoxal and acridine orange." *Proc Natl Acad Sci USA* 74(11): 4835-8.

Oleykowski, C. A., C. R. Bronson Mullins, et al. (1998). "Mutation detection using a novel plant endonuclease." *Nucleic Acids Res* 26(20): 4597-602.

Ravnik-Glavac, M., D. Glavac, et al. (1994). "Sensitivity of single-strand conformation polymorphism and heteroduplex method for mutation detection in the cystic fibrosis gene." *Hum Mol Genet* 3(5): 801-7.

Sainz, J., D. P. Huynh, et al. (1994). "Mutations of the neurofibromatosis type 2 gene and lack of the gene product in vestibular schwannomas." *Hum Mol Genet* 3(6): 885-91.

Sambrook, J. and D. W. Russell (2001). *Molecular cloning: a laboratory manual*. Cold Spring Harbor, N.Y., Cold Spring Harbor Laboratory Press.

Spano, M., J. P. Bonde, et al. (2000). "Sperm chromatin damage impairs human fertility. The Danish First Pregnancy Planner Study Team." *Fertil Steril* 73(1): 43-50.

Tinland, B., N. Pernodet, et al. (1996). "Field and pore size dependence of the electrophoretic mobility of DNA: a combination of fluorescence recovery after photobleaching and electric birefringence measurements." *Electrophoresis* 17(6): 1046-51.

Viovy, J.-L. (2000). "Electrophoresis of DNA and other polyelectrolytes: Physical mechanisms." *Reviews of Modern Physics* 72(3): 813-72.

Yao, M. and Y. W. Kow (1994). "Strand-specific cleavage of mismatch-containing DNA by deoxyinosine 3'-endonuclease from *Escherichia coli.*" *J Biol Chem* 269(50): 31390-6.

The invention claimed is:

1. A method to separate single- from double-stranded non-circular nucleic acid molecules from a mixture, comprising the steps of:
   providing a sample of nucleic acid molecules;
   loading said sample in an electrophoresis gel and electrophoresing in a first dimension said sample using conditions. wherein double-stranded nucleic acid fragments remain intact but conformational differences including local intramolecular secondary structures of single-stranded nucleic acid fragments are minimized, allowing separation of equally long single- and double-stranded nucleic acid molecules;
   denaturing said sample in said gel such that strand separation of double-stranded nucleic acids is obtained, by incubating said gel with a denaturing agent and/or at an elevated temperature above the estimated melting temperature of the sample nucleic acid fragments;
   electrophoresing said gel in a second dimension under conditions that prevent re-formation of double strands, to separate the fractions of single-stranded and double-stranded nucleic acids in the gel.

2. The method of claim 1 wherein one or more denaturing agent(s) is added to the gel prior to the first dimension electrophoresis in a concentration such, that conformational differences between double-stranded nucleic acids are minimized but double-stranded nucleic acid fragment remain intact and such that local intramolecular secondary structures of single-stranded nucleic acid fragments are minimized.

3. The method according to claim 1 or 2, wherein said one or more denaturing agent(s) is selected from the group consisting of aliphatic alcohols; cyclic alcohols; alicyclic compounds; amides; urea or urea-related compounds; carbamates detergents; cyanoguanidine, sulfamide, glycine, dimethyl sulfoxide and acetonitrile.

4. The method according to claim 3, wherein, the aliphatic, alcohol is selected from the group consisting of methyl, ethyl, isopropyl, n-propyl, allyl, butyl, isobutyl alcohol, amyl alcohol and ethylene glycol; the cyclic alcohol is selected from the group consisting of cyclohexyl, benzyl, phenol, and p-methoxyphenol alcohol and inositol; the alicyclic compound is selected from the group consisting of aniline, pyridine, purine, 1,4-dioxane, butyrolactone, and aminotriazole; the amide is selected from the group consisting of foramide, ethylformamide, dimethylformamide, acetamide, N-ethylacetamide N,N-dimethylacetamide, propionamide, glycolamide, thioacetamide, and valerolactam; the urea or urea-related compound is selected from the group consisting of carbohydrazide, 1,3-dirmethylurea, ethylurea, t-butylurea, thiourea, and allylthiourea; the carbamate is selected from the group consisting of urethane, N-methylurethane and N-propylurethane; and the detergent is selected from Tween 40 and Triton X-100.

5. The method according to claim 1, further comprising estimating the length distribution within one or more of said single-stranded and double-stranded fractions after their separation.

6. The method according to claim 1, further comprising analyzing the relative amounts of single-stranded and double-stranded nucleic acid molecules after their separation.

7. The method according to claim 1, further comprising the step of isolating at least a part of said separated nucleic acid fragments from the gel.

8. The method according to claim 1, wherein said sample comprises nucleic acid fragments selected from DNA, RNA, DNA/RNA hybrids cDNA, PNA, PNA/DNA hybrids, or PNA/RNA hybrids or mixtures of any of the above mentioned nucleic acids.

9. The method according to claim 1, wherein double-stranded DNA:DNA helices are separated from double-stranded DNA:RNA hybrids.

10. The method according claim 1, wherein the acid sample is derived from a genome or transcriptome froth one or more individuals.

11. The method according to claim 1, wherein the nucleic acid sample comprises cDNA prepared from one or more individuals.

12. The method according to claim 1, wherein the said nucleic acid sample is a genomic representation comprising a subset of genomic sequences prepared from one or more individuals.

13. A method to measure the renaturation efficiency of a nucleic acid sample subjected to denaturation and renaturation, comprising the steps of the method according to claim 1, wherein the observed relative amount of single- and double-stranded nucleic acid fragments is quantified, following the separation.

14. A method to characterize strandness of products after nucleic acid amplification, wherein following the amplification, single- and double-stranded nucleic acid molecules are separated using the method according to claim 1 wherein the observed relative amounts of single- and double-stranded nucleic acid fragments are quantified and the length distribution of each fraction determined.

15. A method to estimate the efficiency of either first or second strand cDNA synthesis or both, wherein following cDNA synthesis, the cDNA sample is separated using the method according to claim 1, wherein the strandness-dependent separation reveals the amount of single-stranded cDNA, double-stranded cDNA, and RNA:DNA hybrids; and the length distribution of each of the three fractions.

16. A method to normalize a nucleic acid sample comprising separating single- and double-stranded nucleic acid molecules in said sample with the method of claim 1, and further to estimate the amount of single-stranded cDNA, double-stranded nucleic acids and the length distribution of both fractions, and isolating from the gel the single-stranded fraction to obtain normalized material.

17. A method to detect bulge-containing DNA, fragments from a complex DNA sample comprising treating the sample with an agent that cleaves a bulging strand in a bulge-containing double-stranded nucleic acid molecule and subsequently separating single- and double-stranded nucleic acid molecules in with the method of claim 1, wherein the strandness-dependent separation reveals the presence of bulge-containing DNA fragments.

18. A method to detect single-stranded breaks in a complex nucleic acid sample, comprising the method of claim 1, wherein the strands containing breaks give rise to two or more fragments after the denaturation step, which are shorter than intact strands from double-stranded molecules of equal length and are thereby resolved from nucleic: acid fragments with no breaks.

19. A method for mutation-scanning of complex nucleic acid samples, comprising:
   providing a nucleic acid sample/pool from one or more individuals,
   denaturing the DNA sample/pool such that double strands are separated,
   renaturing said sample/pool of DNA samples to form nucleic acid heteroduplexes comprising homologous strands, treating said mixture of renatured nucleic acid with an agent that specifically induces a single-stranded break at a mismatch, separating duplexes containing single-stranded breaks from intact duplexes by the method of claim 18.

20. A method to detect lesions in complex nucleic acid samples, comprising:

providing nucleic acid sample that comprises nucleic acids from one or more individuals, treating said sample of nucleic acid duplexes with an enzyme or agent that specifically induces single-stranded breaks in a presence of a lesion;

separating duplexes containing, single-stranded breaks from intact duplexes by the method of claim 18.

21. The method of claim 1, wherein the electrophoresing is carried out with an electrophoresis system that comprises:

an electrophoresis cassette for supporting a gel sandwiched between supporting plates, an electrophoresis apparatus with a compartment for fitting said, electrophoresis cassette, and a sample port for introducing a sample to said cassette, a first set of electrodes, to sustain a first electrical field across a gel in an inserted cassette, when electrical power is applied to said electrodes, a second set of electrodes to sustain a second electrical field across the gel essentially orthogonal to said first electrical field, when electrical power is applied to said electrodes, and heating means having a heating surface within said compartment to provide heat to and sustain said gel substantially at a pre-determined temperature.

22. The method of claim 21, wherein said electrophoresis system further comprises a power supply and a computer loaded with computer software to control operation of said system, said controlling includes applying a first voltage to said first set of electrodes for a period of time, while the gel is maintained a first pre-determined temperature; raising the temperature of the gel to a second pre-determined temperature for a period of time. and applying a second voltage to said second set of electrodes for a period of time.

23. The method of claim 21, wherein said electrophoresis system is configured to sustain and withstand operating temperatures of at least 75° C.

24. The method of claim 21, wherein said electrophoresis system is configured to sustain and withstand operating temperatures of at least 90° C.

25. The method of claim 21, wherein said electrophoresis system is a microsystem configured to operate with microgels of a size smaller than 10 cm$^2$.

26. The method of claim 21, wherein said electrophoresis system further comprises computer software loaded on a computer, for analyzing a gel electrophoresed according to the method, based on a digitized image of said gel stained with a suitable detecting agent, said computer software comprising code such that when run by a computer, steps are performed to detect spots corresponding to internal standards, detect stained areas and determine boundaries of said areas, based on the location of the internal standards spots, assign detected areas as single-stranded or double-stranded nucleic acids, and estimate density of detected areas and integrate to determine ratio of single-stranded vs. double-stranded nucleic acids in the electrophoresed gel.

27. The method of claim 26, wherein said computer software further comprises code such that steps are performed to estimate the length distribution of one or more of the separated fractions, based on the spatial distribution within the gel image of the detected fraction areas.

28. A computer program product loadable on a computer, for analyzing an image of a two-dimensional electrophoresis gel to determine the ratio of single-stranded and double-stranded nucleic acids in a sample run in said gel, said computer program product comprising program instruction means to instruct a computer processor when loaded and run on a computer, to:

receive input values defining internal standards in said sample comprising both single-stranded and double-stranded nucleic acids in differing known length, detect spots in said image corresponding to said internal standards, detect stained areas and determine boundaries of said areas, based on the location of the internal standards spots, assign detected areas as single-stranded or double-stranded nucleic acids, estimate density of detected areas and integrate to determine ratio of single-stranded vs. double-stranded nucleic acids in the electrophoresed gel.

29. The computer program product of claim 28 further comprising program instruction means to instruct a computer processor when loaded and run on a computer to estimate the length distribution within one or more of said single-stranded and double-stranded fractions.

* * * * *